United States Patent
Maidment et al.

(10) Patent No.: US 11,786,186 B2
(45) Date of Patent: *Oct. 17, 2023

(54) SUPER-RESOLUTION TOMOSYNTHESIS IMAGING SYSTEMS AND METHODS

(71) Applicants: The Trustees Of The University Of Pennsylvania, Philadelphia, PA (US); Real Time Tomography, LLC, Villanova, PA (US)

(72) Inventors: Andrew D. A. Maidment, Villanova, PA (US); Raymond J. Acciavatti, Newtown Square, PA (US); Susan Ng, Villanova, PA (US); Peter A. Ringer, Allentown, PA (US); Johnny Kuo, Lancaster, PA (US)

(73) Assignees: The Trustees of the University of Pennsylvania, Philadelphia, PA (US); Real Time Tomography, LLC, Villanova, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/535,131

(22) Filed: Nov. 24, 2021

(65) Prior Publication Data
US 2022/0160312 A1 May 26, 2022

Related U.S. Application Data

(63) Continuation of application No. 15/443,737, filed on Feb. 27, 2017, now Pat. No. 11,185,294.
(Continued)

(51) Int. Cl.
*A61B 6/02* (2006.01)
*A61B 6/00* (2006.01)
*G01N 23/046* (2018.01)

(52) U.S. Cl.
CPC ............. *A61B 6/025* (2013.01); *A61B 6/461* (2013.01); *A61B 6/502* (2013.01); *A61B 6/54* (2013.01); *G01N 23/046* (2013.01)

(58) Field of Classification Search
CPC .......... A61B 6/027; A61B 6/54; A61B 6/461; A61B 6/502; A61B 6/4452; A61B 6/025;
(Continued)

(56) References Cited

U.S. PATENT DOCUMENTS

| 7,817,773 B2 | 10/2010 | Stanton et al. |
| 8,233,690 B2 | 7/2012 | Ng et al. |

(Continued)

FOREIGN PATENT DOCUMENTS

| JP | 10-314161 A | 12/1998 |
| WO | 2012/077694 A1 | 6/2012 |
| WO | 2014/011681 A3 | 3/2014 |

OTHER PUBLICATIONS

Abstract of Disclosure 16-78114 Modeling Acquisition Geometries with Improved Super-Resolution in Digital Breast Tomosynthesis, dated Oct. 30, 2015, 1 page.
(Continued)

*Primary Examiner* — Irakli Kiknadze
(74) *Attorney, Agent, or Firm* — BakerHostetler

(57) ABSTRACT

A super-resolution digital tomosynthesis system for imaging an object including a source configured to emit penetrating particles toward an object; a detector configured to acquire a series of projection images of the object in response to the penetrating particles from the source; positioning apparatus configured to position the source and the detector; and an imaging system coupled to the source, the detector, and the positioning apparatus. The imaging system is configured to control the positioning apparatus to position the source in relation to the detector along a scan path and to change a (Continued)

distance between the source and the detector, control the source and the detector to acquire the series of projection images along the scan path with the distance change between the source and detector, and construct a tomographic volume exhibiting super-resolution from data representing the acquired series of projection images.

24 Claims, 33 Drawing Sheets

Related U.S. Application Data

(60) Provisional application No. 62/300,290, filed on Feb. 26, 2016.

(58) Field of Classification Search
CPC ....... A61B 6/0414; A61B 6/032; A61B 6/466; A61B 6/14; A61B 6/584; A61B 6/4241; A61B 6/582; A61B 6/482; A61B 6/5252; A61B 6/425; A61B 6/583; A61B 6/5205; A61B 6/542; A61B 6/4064; A61B 6/4291; A61B 6/484; A61B 6/06; A61B 6/4085; A61B 8/5207; A61B 6/4007; A61B 6/4208; A61B 6/4233; A61B 6/4441; A61B 6/507; A61B 6/486; A61B 6/481; A61B 6/5235; A61B 6/505; A61B 6/4435; A61B 6/40; A61B 6/4078; A61B 6/463; A61B 6/5241; G01N 23/046; G01N 23/044; G01N 2223/401; G06T 11/003; G06T 11/006; G06T 11/005; G06T 2210/41; G06T 7/0012; H04N 5/32; H04N 5/347
USPC .................................................. 378/4, 22, 62
See application file for complete search history.

(56) References Cited

U.S. PATENT DOCUMENTS

| | | | |
|---|---|---|---|
| 8,391,581 B2 | 3/2013 | Masuda et al. | |
| 8,509,512 B2 | 8/2013 | Ota et al. | |
| 9,743,891 B2 | 8/2017 | Maidment et al. | |
| 11,185,294 B2* | 11/2021 | Maidment | A61B 6/502 |
| 2002/0110303 A1* | 8/2002 | Werkheiser | G02B 6/4225 |
| | | | 385/2 |
| 2002/0176540 A1 | 11/2002 | Sakaida | |
| 2005/0175143 A1 | 8/2005 | Miyazaki et al. | |
| 2005/0226369 A1 | 10/2005 | Martin et al. | |
| 2010/0067822 A1 | 3/2010 | Young | |
| 2011/0026667 A1 | 2/2011 | Poorter | |
| 2011/0069812 A1 | 3/2011 | Takahashi | |
| 2011/0155660 A1 | 6/2011 | Mickols et al. | |
| 2011/0255660 A1 | 10/2011 | Masuda et al. | |
| 2012/0014498 A1 | 1/2012 | Akahori | |
| 2014/0294138 A1* | 10/2014 | Jerebko | A61B 6/5258 |
| | | | 378/4 |
| 2016/0042537 A1 | 2/2016 | Ng et al. | |
| 2016/0302742 A1* | 10/2016 | Maidment | A61B 6/481 |
| 2017/0055927 A1* | 3/2017 | Palma | A61B 6/469 |

OTHER PUBLICATIONS

Acciavatti et al., "Calculation of OTF, NPS, and DQE for Oblique X-Ray Incidence on Turbid Granular Phosphors", 2010, LNCS 6136, pp. 436-443.

Acciavatti et al., "Investigating the Potential for Super-Resolution in Digital Breast Tomosynthesis", University of Pennsylvania—Mar. 2016, 12 pages.

Acciavatti et al., "Modeling Acquisition Geometries with Improved Super-Resolution in Digital Breast Tomosynthesis", Perelman School of Medicine at the University of Pennsylvania—Mar. 2016, 12 pages.

Acciavatti et al., "Observation of Super-Resolution in Digital Breast Tomosynethesis", Med. Phys. vol. 39, No. 12, Dec. 2012—pp. 7518-7539.

Acciavatti et al., "Optimization of phosphor-based dectector design for oblique x-ray incidence in digital breast tomosynthesis", Med. Phys. vol. 38, No. 11, Nov. 2011—pp. 6188-6202.

Acciavatti et al., "Optimizing the Acquisition Geometry for Digital Breast Tomosynthesis Using Defrise Phantom", Medical Imaging 2014: Physics of Medical Imaging, edited by Bruce R. Whiting, Christoph Hoeschen, Despina Kontos, Proc. of SPIE, 2014, vol. 9033—12 pages.

Acciavatti et al., "Proposing an Acquisition Geometry that Optimizes Super-Resolution in Digital Breast Tomosynthesis", 2012, LNCS 7361, pp. 386-393.

Badano et al., "Oblique incidence effects in direct x-ray detectors: A first-order approximation using a physics-based analytical model", Med. Phys., vol. 38, No. 4, Apr. 2011—5 pages.

Dziok et al., "Certain results for a class of convex functions related to a shell-like curve connected with Fibonacci numbers", Computer and Mathematics with Applications, vol. 61 (2011) pp. 2605-2613.

Freed et al., "A fast angle-dependent, analytical model of CsI detector response for optimization of 3D x-ray breast imaging systems" Med. Phys. vol. 37, No. 6, Jun. 2010, pp. 2593-2605.

Friedwald et al., "Breast Cancer screening using tomosynthesis in combination with digital mammography", JAMA, 2014; vol. 311, No. 24, pp. 2499-2507.

International Search Report and Written Opinion for International Application No. PCT/US2013/049789, dated Dec. 30, 2013, 8 pages.

Kuo et al., "Dynamic reconstruction and rendering of 3D Tomosynthesis images", Med. Imaging 2011: Physics of Medical Imaging, Proc. of SPIE, vol. 7961, 72014,—11 pages.

Lee et al., "Improved imaging performance of a 14 x 17-inch Direct Radiograph tm System using Se/TFT detector", Proc. of SPIE, vol. 3336, Medical Imaging 1998: Physics of Medical Imaging, (May 1998)—pp. 14-23.

Maidment et al., "Construction of a prototype digital breast tomosynthesis system with superior spatial resolution", powerpoint presentation, University of Pennsylvania, 2012—27 pages.

Mazin et al., "Fourier rebinning algorithm for inverse geometry CT", Med. Phys. vol. 35, No. 11, Nov. 2008—pp. 4857-4862.

Pokrajac et al., "Optimized generation of high resolution breast anthropomorphic software phantoms", Med. Phys., vol. 39, No. 4, Apr. 2012—pp. 2290-2302.

Poplack et al., "Digital breast Tomosynthesis: Initial experience in 96 women with abnormal digital screening mammography", AJR: 189, Sep. 2007—pp. 616-623.

Rafferty et al., "Assessing radiologist performance using combined digital mammography and breast Tomosynthesis compared with digital mammography alone: Results of a multicenter, multireader trial", radiology.rsna.org, Radiology vol. 266, No. 1—Jan. 2013—pp. 104-113.

Rafferty, E., "Tomosynthesis: New weapon in breast cancer fight", http://www.axisimagingnews.com/2004/04/tomosynthesis-new-weapon-in-breast-cancer-fight, 2004—2 pages.

Zhao et al., "Three-Dimensional linear system analysis for breast tomosynthesis", Med. Phys. vol. 35, No. 12, Dec. 2008—pp. 5219-5232.

* cited by examiner

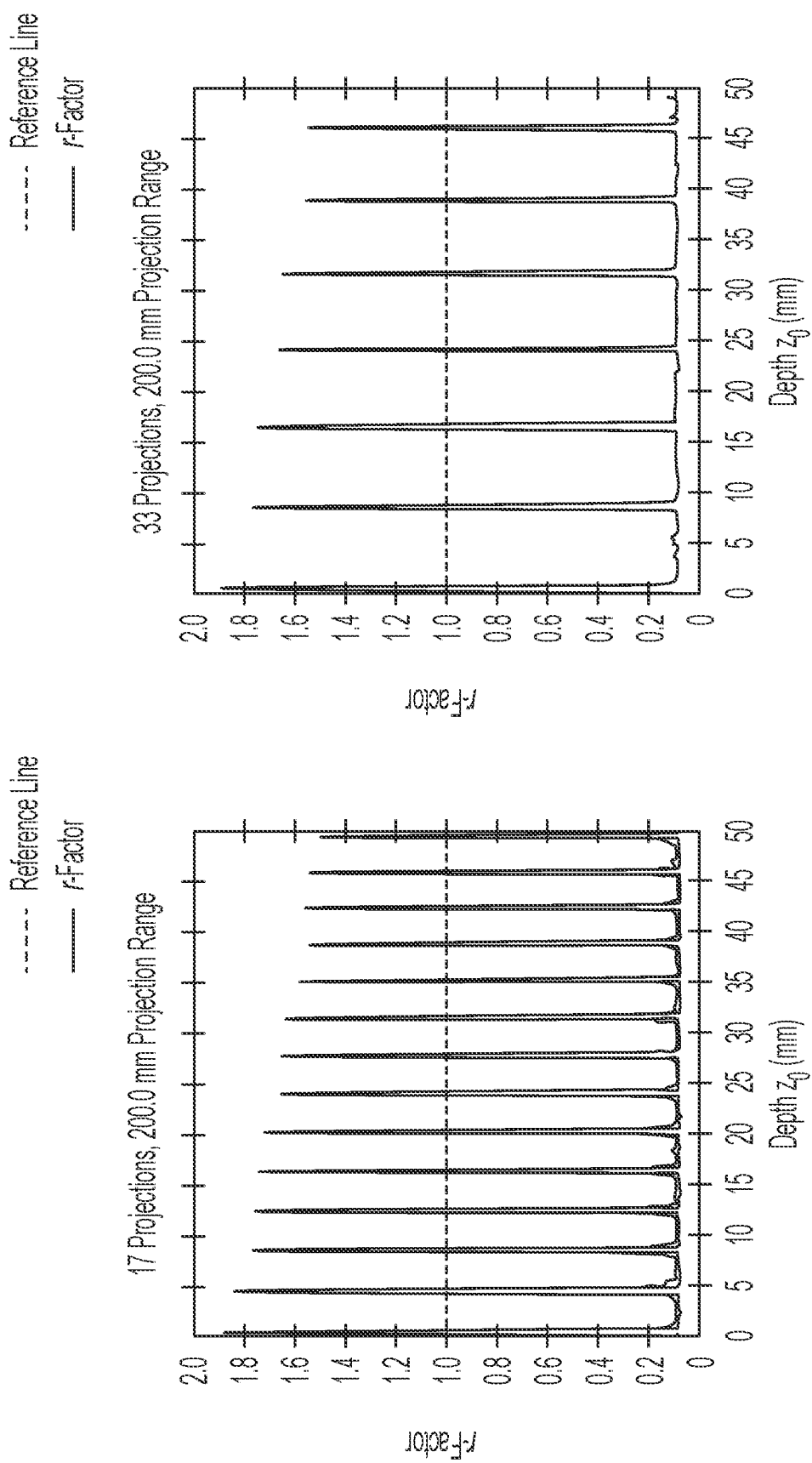

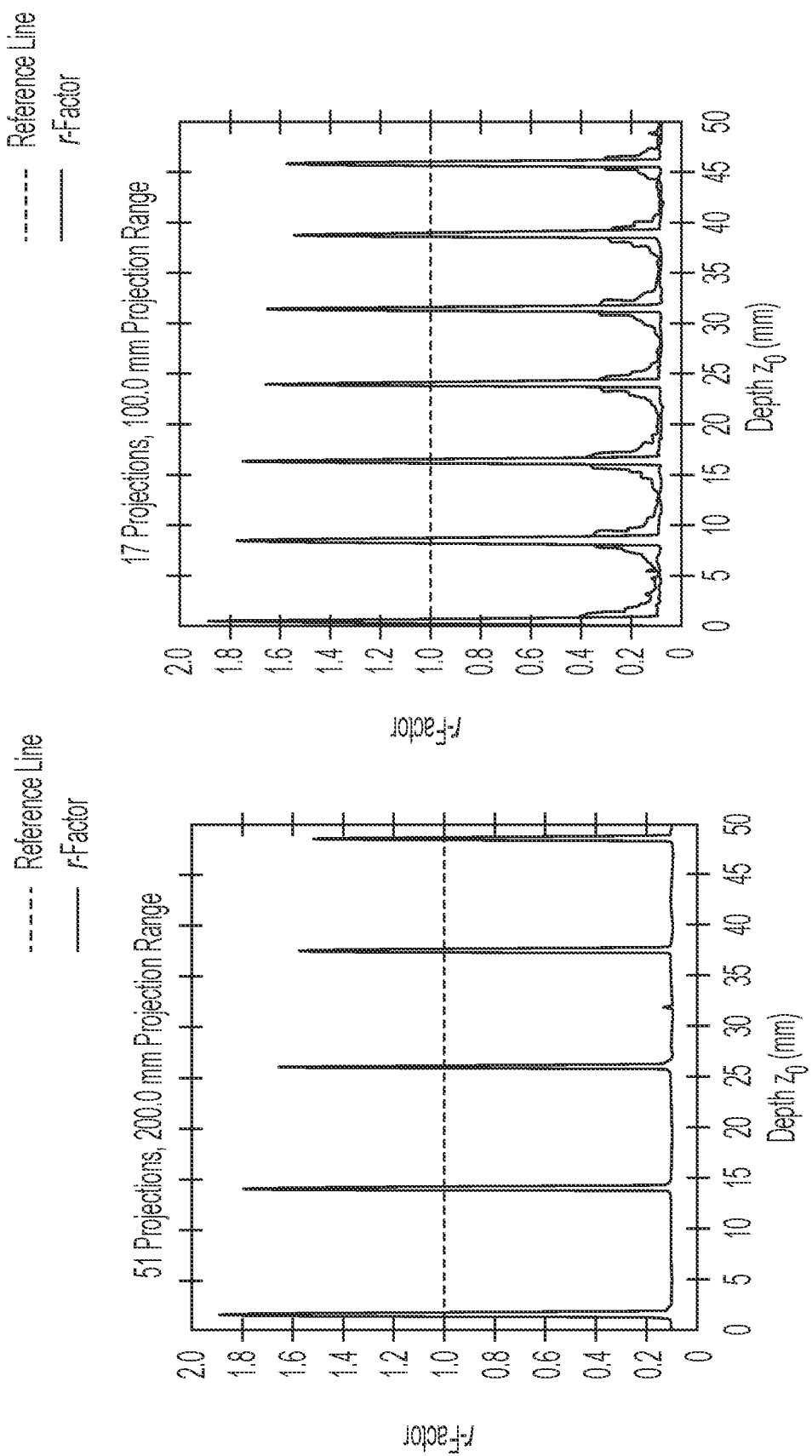

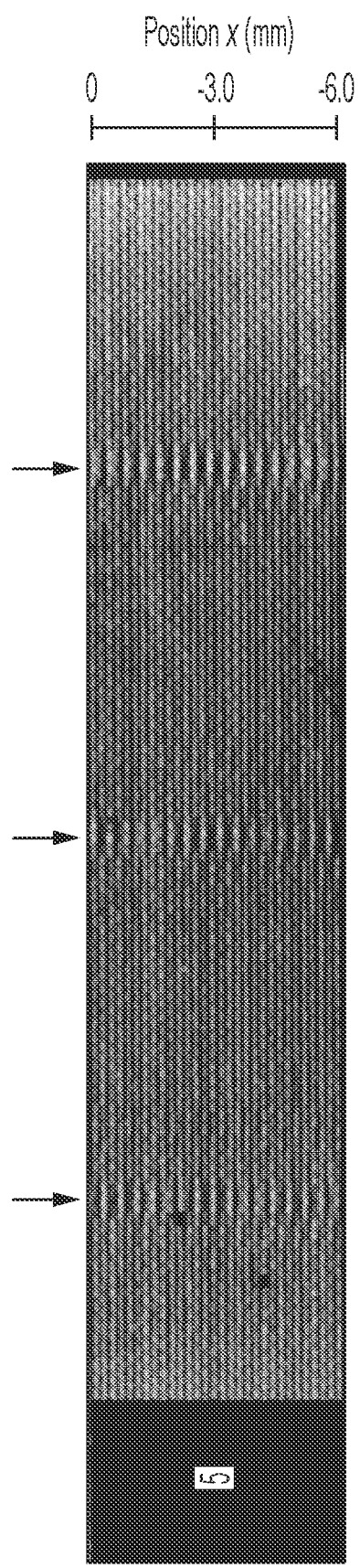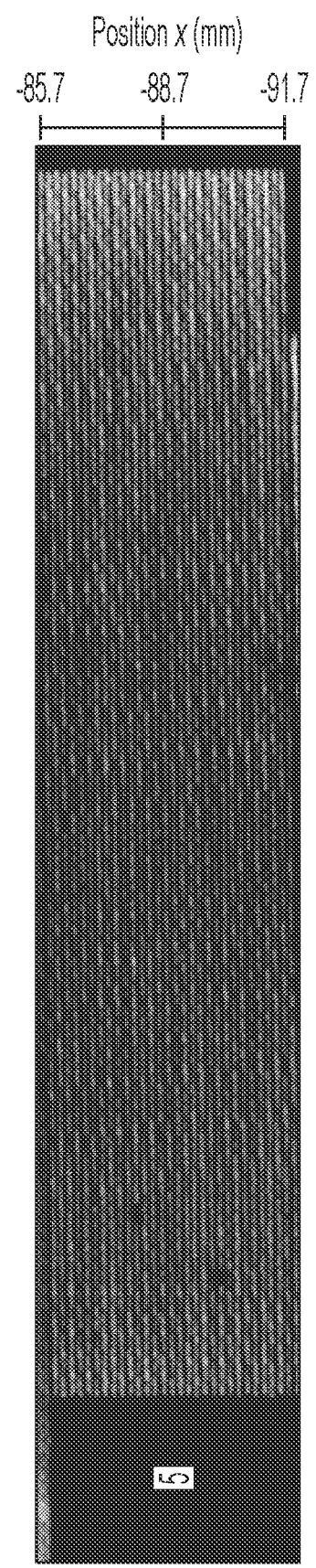
FIG. 14A
FIG. 14B

SUPER-RESOLUTION TOMOSYNTHESIS IMAGING SYSTEMS AND METHODS

CROSS-REFERENCE TO RELATED APPLICATIONS

This application is a continuation application of U.S. patent application Ser. No. 15/443,737, filed Feb. 27, 2017, which claims the benefit of U.S. Provisional Patent Application No. 62/300,290, filed Feb. 26, 2016, each of which is incorporated herein by reference in its entirety for any and all purposes.

BACKGROUND INFORMATION

In digital tomosynthesis (DT), a 3-dimensional image of an object or anatomy is typically generated from a limited number of low-dose x-ray projections acquired from different angles. The x-ray source is typically moved in an arc around an object being imaged (such as a breast) while a series of projection images are captured with a detector including an array of pixels. The arc is along a scan direction that is aligned with rows of pixels within the pixel array. Data from the resultant projection images is then processed by a computer to create a 3-dimensional tomographic volume. In breast imaging, digital breast tomosynthesis (DBT) has been shown to improve sensitivity and specificity for cancer detection relative to traditional two-dimensional projection mammography. In chest imaging, DT has been shown to improve the sensitivity and specificity of lung nodule detection relative to traditional two-dimensional projection radiography. DT has also had value in musculoskeletal imaging and in non-destructive testing.

DT's oblique x-ray incidence shifts the image of features within an object in sub-pixel detector element increments along the scan direction with each projection angle. As a result of this property, DT is capable of "super-resolution", a term which is used to denote sub-pixel resolution, i.e., resolution that is finer than the physical size of the detector elements. Although super-resolution is achievable over a broad range of positions along the scan direction (e.g., parallel to the chest wall side of the breast support in current DBT systems), it cannot be achieved over as broad of a range of positions perpendicular to the scan direction (e.g., the chest wall—nipple direction in current DBT systems).

Higher resolution images are useful in the accurate detection and diagnosis of cancer, bone fractures, and other fine details. In breast imaging, for example, the presence of lesions, such as microcalcifications, can indicate the early stage of breast cancer. The form and morphology of the microcalcifications are important factors in determining whether the microcalcifications are benign or malignant. Improved visibility and conspicuity of lesions help in the determination of the probability of malignancy. It is therefore desirable to determine and set acquisition parameters to optimize super-resolution.

SUMMARY OF THE INVENTION

Super-resolution tomosynthesis imaging methods, systems, and apparatus are disclosed. An embodiment of a super-resolution digital tomosynthesis system for imaging an object includes a source configured to emit penetrating particles toward an object; a detector configured to acquire a series of projection images of the object in response to the penetrating particles from the one source; positioning apparatus configured to position the source and the detector; and an imaging system coupled to the source, the detector, and the positioning apparatus. The imaging system is configured to control the positioning apparatus to position the source in relation to the detector along a scan path and change a distance between the source and the detector; control the source and the detector to acquire the series of projection images along the scan path with the distance change between the source and detector; and construct a tomographic volume exhibiting super-resolution from data representing the acquired series of projection images.

An embodiment of a super-resolution digital tomosynthesis method for imaging an object includes positioning a source of penetrating particles along a scan path with respect a detector, changing a distance between the source and the detector as the source is positioned along the scan path; acquiring a series of images along the scan path with the change of the distance between the source and the detector; and constructing a tomographic volume exhibiting super-resolution from data representing the acquired series of projection images.

BRIEF DESCRIPTION OF THE DRAWINGS

The invention is best understood from the following detailed description when read in connection with the accompanying drawings, with like elements having the same reference numerals. When a plurality of similar elements are present, a single reference numeral may be assigned to the plurality of similar elements with a small letter designation referring to specific elements. When referring to the elements collectively or to a non-specific one or more of the elements, the small letter designation may be dropped. Also, lines without arrows connecting components may represent a bi-directional exchange between these components. This emphasizes that according to common practice, the various features of the drawings are not drawn to scale. On the contrary, the dimensions of the various features are arbitrarily expanded or reduced for clarity. Included in the drawings are the following figures:

FIGS. 11A-11F are graphs of r-factor plotted as a function of depth for simulations using varying numbers of projections and varying angular ranges between such projections in accordance with a conventional acquisition geometry for tomosynthesis;

FIGS. 14A and 14B are images of reconstruction planes aligned with the oblique plane of the bar pattern of FIG. 13 in accordance with a conventional acquisition geometry for tomosynthesis;

DESCRIPTION OF THE INVENTION

Aspects of the present invention provide for improved tomosynthesis systems for providing super-resolution imaging of an object. As discussed further herein, the inventors discovered that improved super-resolution images may be obtained (e.g., by changing the distance between a source and the detector during scanning of the object) by varying the magnification of the projected image of the object onto the detector.

The present invention may be used to obtain super-resolution images for objects including inanimate objects, such as luggage, or anatomical features of a living being, such as a lung or a breast.

Figure 1A:
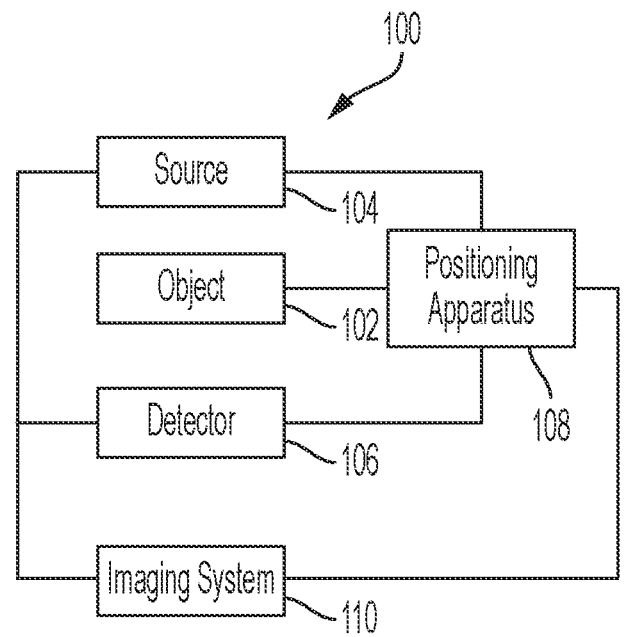
FIG. 1A is a block diagram of a tomosynthesis system for imaging an object in accordance with aspects of the invention.

FIG. 1 depicts a tomosynthesis system 100 for imaging an object 102 in accordance with aspects of the invention. The illustrated system 100 includes a source 104 that emits penetrating particles toward a detector 106, with the object positioned in between the source 104 and the detector 106. Penetrating particles that pass through the object 102 create a projection image of the object on the detector 106. The penetrating particles may be x-rays, photons, neutrons, beta particles, or other particles capable of passing through the object and creating a projection image on a detector 106.

The source 104 may be a conventional x-ray tube configured to emit x-rays toward the object 102 and the detector 106. The detector 106 may be a conventional x-ray detector including an array of pixels. The array of pixels may be square, another geometric shape, a combination of geometric shapes, or irregular. Additionally, the array of pixels may be formed from a two-dimensional array of pixels or a series of one-dimensional arrays of pixels. Other suitable sources 104 and detectors 106 (e.g., those capable of emitting and detecting other penetrating particles) will be understood by one of skill in the art from the description herein. Additionally, although a single source 104 and a single detector 106 are illustrated, additional sources 104 and detectors 106 may also be employed.

Positioning apparatus 108 is coupled to the object 102 (e.g., via a support member for the object 102, which is described in further detail below), the source 104, and the detector 106. As described in further detail below, the positioning apparatus 108 is configured to position the source 104 relative to the object 102 and the detector 106 along a scan path and to change a distance between the source 104 and the detector 106 by moving the detector 106 substantially perpendicular to the scan path, e.g., in a z-direction. The scan path may be a linear path, an arc path, or a more complex path. An embodiment of a more complex scan path is illustrated in FIGS. 5, 8A, 8B and 8C. Since the source 104 may be moved in an arc, the detector 106 may move in a direction substantially perpendicular to the arc's tangent at the location of the source. As used herein, the term "substantially" refers to a range of values. For example, the phrase "substantially perpendicular" includes ±30 degrees from a true 90 degrees perpendicular with respect to a reference plane, e.g., from 60 degrees to 120 degrees of an arc's tangent.

In use, the source 104 emits penetrating particles at a series of locations along the scan path. The distance between the source 104 and the detector 106 is changed such that the magnification of the projected image of the object as detected by the detector 106 varies as the source 104 travels along the scan path. The variations in the magnification over the range of positions of the source 104 along the scan path of the image of the object enables super-resolution to be obtained throughout the reconstructed volume. In one embodiment, varying the magnification of the projected image of the object by positioning/moving the detector 106 to change the distance between the source 104 and the detector 106 over the entirety of the positions of the source 104 along the scan path obtains super-resolution throughout the reconstructed volume.

In an embodiment, the object 102 remains stationary and the positioning apparatus is coupled to the source 104 to move the source 104 along a scan path and is coupled to the detector 106 to move the detector 106 such that the distance between the source 104 and the detector 106 is changed. Other suitable arrangements that vary the distance between the source 104 and the detector 106 during the acquisition of the projections will be understood by one of skill in the art from the description herein and are considered within the scope of the invention.

An imaging system 110 is coupled to the source 104, the detector 106, and the positioning apparatus 108. The imaging system 110 instructs the positioning apparatus 108 to position the object 102/source 104/detector 106, instructs the source 104 to emit penetrating particles, captures data from the detector 106 representing projection images of the object 102 responsive to the emitted penetrating particles, and constructs a tomographic volume of the object that is capable of exhibiting super-resolution. Additionally, the imaging system may display super-resolution images generated from the tomographic volume. The imaging system 110 may include, for example, user input devices such as a keyboard and a mouse for receiving operator instructions to manipulate images, user output devises such as a display for displaying super-resolution images, and an internal and/or external memory for storing instructions for implementing one or more of the steps described herein, for storing data from acquired images, and for storing constructed tomographic volumes. Suitable input and output devices and memory will be understood by one of skill in the art from the description herein.

Figure 1B:
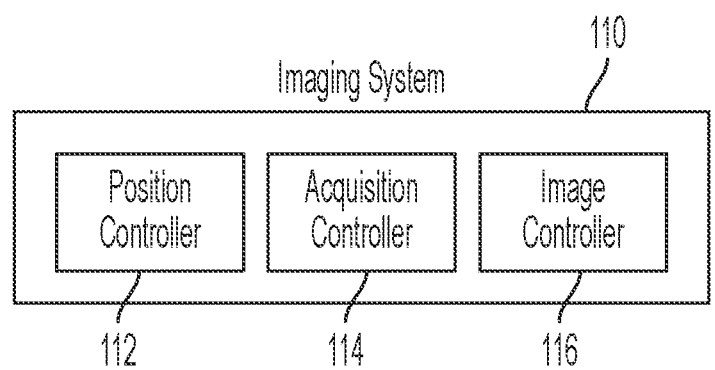
FIG. 1B is a block diagram of an imaging system for use in the tomosynthesis system of FIG. 1A in accordance with aspects of the invention.

As illustrated in FIG. 1B, the imaging system 110 includes a position controller 112, an acquisition controller 114, and an image controller 116. The position controller 112 may control positioning apparatus 108 to position the object 102, the source 104, and/or the detector 106 relative to one another to enable a series of images to be captured along a scan path with a variable magnification of the detected penetrating particles by positioning the detector 106, the source 104, or a combination thereof to change the distance between the source 104 and the detector 106 during the acquisition of the projections.

The acquisition controller 114 may control the source 104 and the detector 106 to respectively emit penetrating particles and capture projected images of the object 102 responsive to the emitted penetrating particles. The acquisition controller may interface with the position controller 112 to ensure the object 102, source 104, and detector 106 are accurately positioned relative to one another during the capture of each of the series of images.

The image controller 116 may process data representing the projected images on the detector 106 to construct a tomographic volume capable of exhibiting super-resolution by taking the scan path and the variable magnification of penetrating detected particles into consideration. Additionally, the image controller 116 may display super-resolution images developed from the tomographic volume.

Although depicted as three separate controllers (position controller 112/acquisition controller 114, and image controller 116) in FIG. 1B, the functionality of these controllers can be performed by more or fewer controllers and/or by one or more processors. Additionally, the controllers/processors may reside in a single housing or may be dispersed across a network.

Figure 2A:
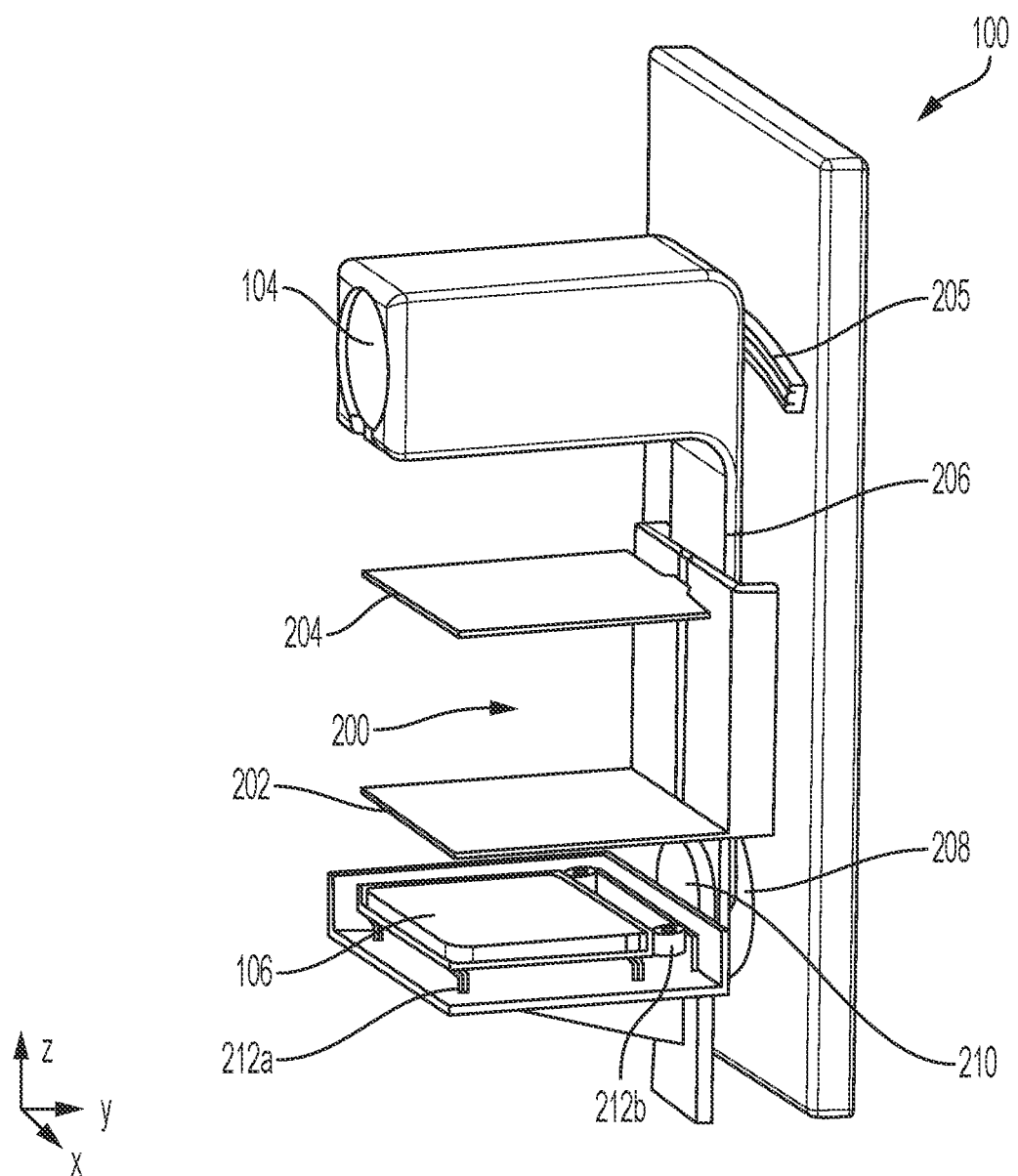
FIG. 2A is a perspective view of a source, detector, and positioning apparatus for use in a tomosynthesis system for imaging an object in accordance with aspects of the invention.
Figure 2B:
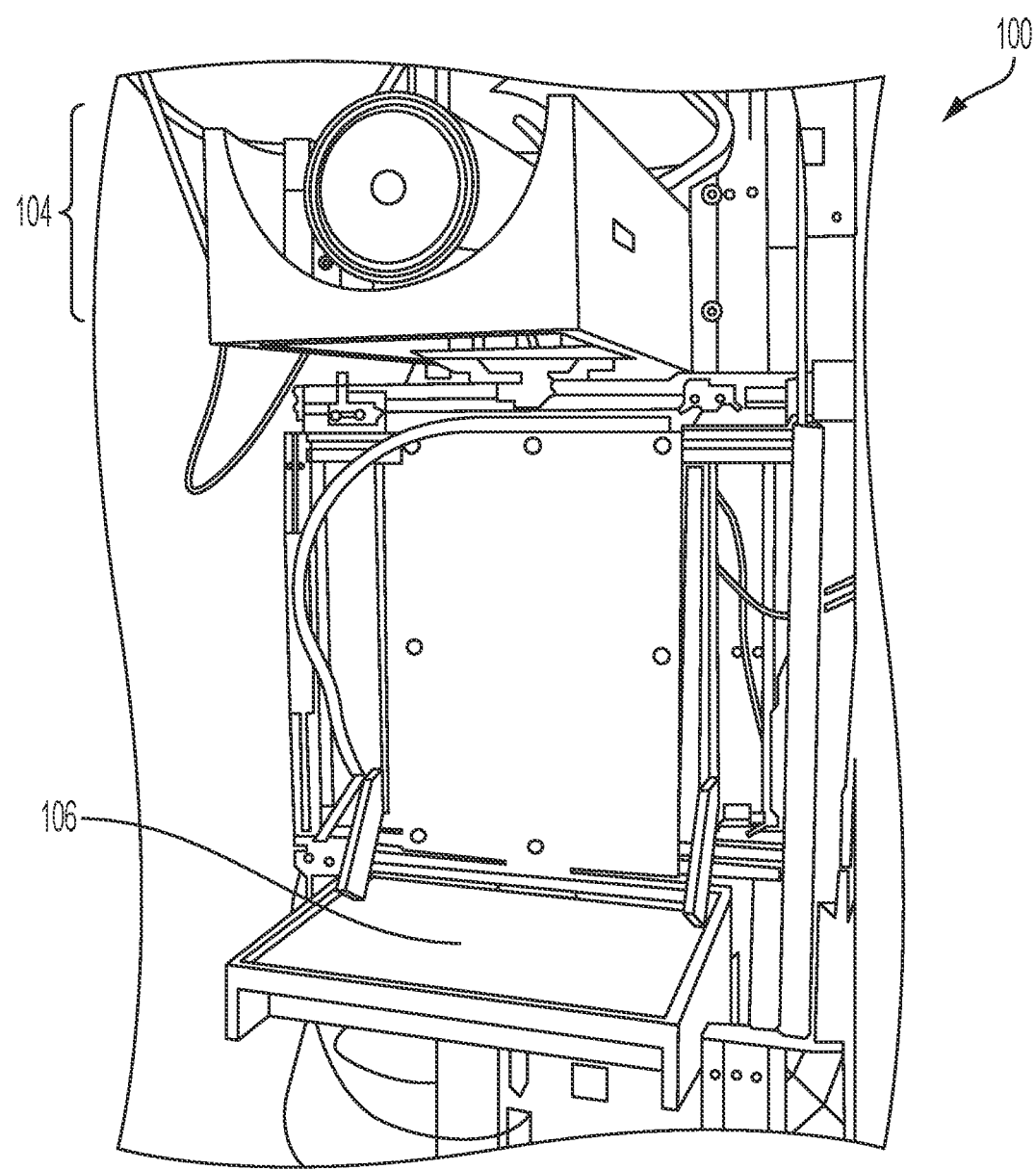
FIG. 2B is a perspective view of an implementation of the tomosynthesis system for imaging an object of FIG. 2A.

FIGS. 2A-2B depict an embodiment of a source 104, detector 106, and positioning apparatus 108 (FIG. 1) for use in imaging a human breast. Suitable modifications will be understood by one of skill in the art from the description herein for imaging other objects.

A breast may be positioned within an object receiving area 200. The illustrated object receiving area 200 includes a breast support 202, and a compression paddle 204. The breast may be positioned on the breast support 202, which is fixed in position, and the compression paddle 204 may be lowered in a conventional manner into contact with the breast to reduce movement of the breast during the acquisition of images. In an embodiment, the breast support 202 and a movable breast compression paddle 204 are mounted orthogonal to a central ray of penetrating particles emitted by the source 104.

The source 104 illustrated in FIG. 2A includes a conventional x-ray tube and the illustrated detector 106 includes a conventional 2-dimensional x-ray detector. The positioning apparatus 108 in the embodiment illustrated in FIG. 2A includes an angular drive 205 (e.g., an electro-mechanical drive) coupled to the source 104 to move the source 104 along a scan path (e.g., an arc in the x/z plane) and micro positioners 212 (e.g., electro-mechanical drivers) for positioning the detector 106. Micro-positioners 212a are coupled to the detector 106 to position the detector 106 in order to change a distance between the source 104 and the detector 106, e.g., in the z-direction to vary the magnification of the projected image of the object. Additional micro-positioners, such as micro-positioners 212b, may be used to position the detector 106 in other directions to, e.g., introduce an offset in one or more directions, such as in the y-direction. In one embodiment, four micro-positioners 212a (one at each corner of detector 106) are configured to position the detector 106 in the z-direction, while micro-positioners 212b are configured to position the detector 106 in the y-direction. The addition of micro-positioners 212 allows sub-pixel positioning accuracy for the array of pixels in detector 106. The micro-positioners 212 may be amplified piezoelectric actuators. Super-resolution can be optimized by considering the acquisition geometry and the system components.

In one embodiment, the micro-positioners 212, with the detector 106 positioned thereon, are coupled to a rotary stage 210 having an axis of rotation that extends along a detection surface of the detector 106. The rotary stage 210 rotates on a slewing bearing 208 that supports the load of the object receiving area 200, the source 104, the detector 106, and the micro-positioners 212. A rotary arm 206 is positioned between the source 104 and the detector 106. Although the axis of rotation is illustrated as extending along the surface of the detector 106, other axes of rotations may be employed, e.g., one extending though the object being imaged. In other embodiments, the scan path may be linear.

Figure 3:
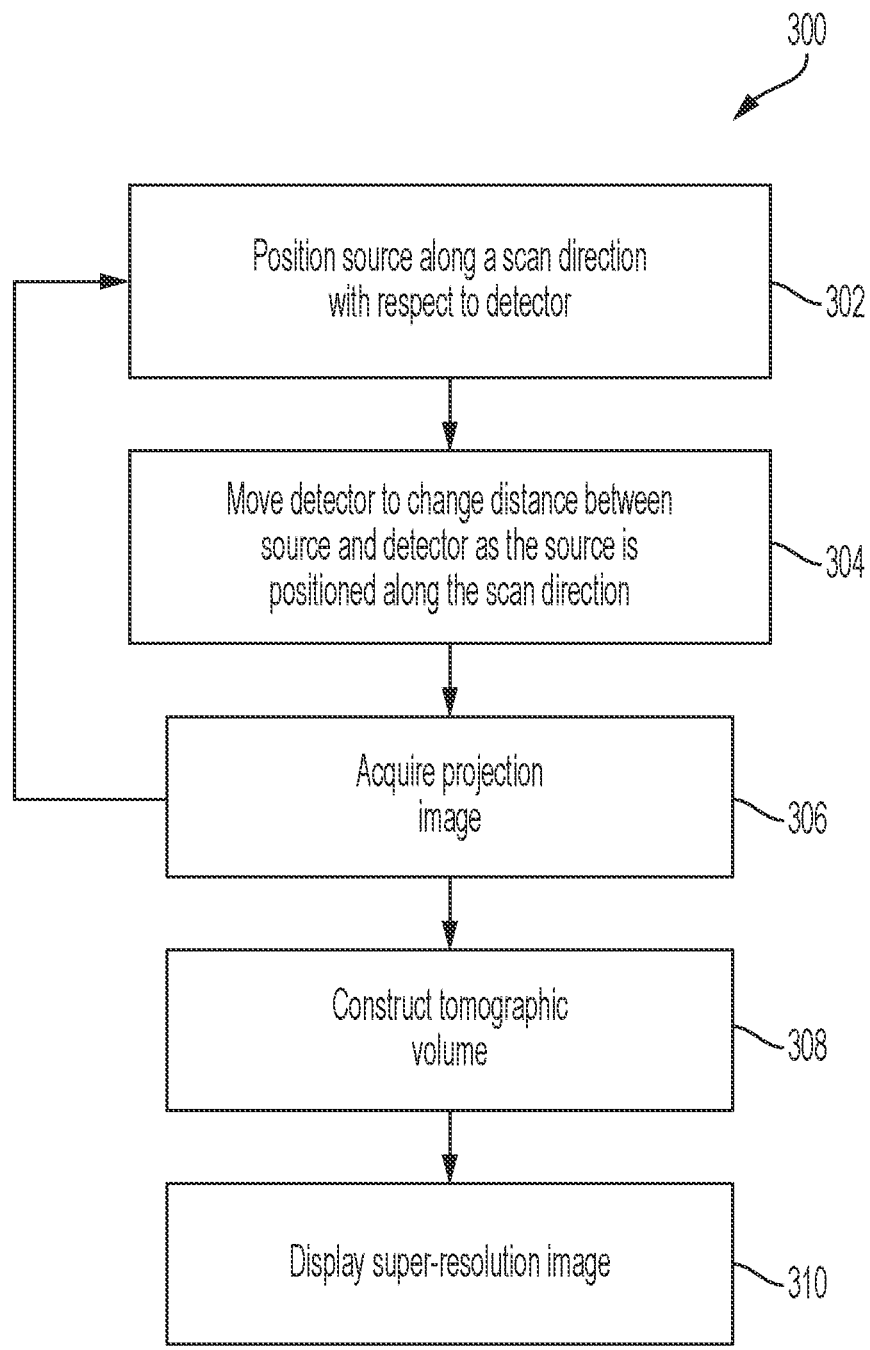
FIG. 3 is a flow chart of tomosynthesis imaging steps for imaging an object in accordance with aspects of the invention.

FIG. 3 depicts a flow chart 300 of exemplary steps for constructing a tomographic volume capable of exhibiting super-resolution by taking the scan path and the variable magnification of the projected image of the object into consideration. Although the steps of flow chart 300 are described with reference to the apparatus depicted in FIGS. 1A, 1B, and 2, it will be understood that other apparatus may be used in accordance with the invention. Likewise, the apparatus depicted in FIGS. 1A, 1B, and 2 may perform other methods. Additionally, in some embodiments, one or more steps of flow chart 300 may be omitted or performed in an order other than depicted (including at the same time).

At block 302, a source is positioned with respect to an object and a detector along a scan path. The source may be source 104 and the detector may be detector 106. In one embodiment, the source 104 is configured to move along a scan path with respect to the object 102 and the detector 106. For example, when imaging a breast, the source 104 may be moved along a scan path that is an arc within a plane substantially parallel to the chest wall. In this example, the breast remains stationary during the imaging and the detector 106 may remain stationary or may move such that the detecting surface of the detector 106 is normal to the penetrating rays emitted by the source 104.

At block 304, the detector is moved to change a distance between the source (e.g., source 104) and the detector (e.g., detector 106). By changing the distance between the source 104 and the detector 106 as the source 104 is positioned/moved along the scan path, variable magnification of the projected image of the object as detected by the detector 106 may be obtained. For example, when imaging a breast, the detection surface of the detector 106 may be moved in a z-direction, e.g., directly towards or away from the object 102, to change the distance between the source 104 and the detector 106. In one embodiment, the z-direction is substantially parallel to the plane of the chest wall, such as in a breast imaging application. In another embodiment, the z-direction is directly towards or away from the object 102 and/or source 104.

The detector 106 may be moved to change the distance between the source 104 and the detector 106 at the same time as the positioning is performed in step 302. Alternatively, steps 302 and 304 may be performed sequentially in steps. The movement of the source 104 and the detector 106 for positioning along the scan path (step 302) and/or to change the distance between the source 104 and the detector 106 may be a continuous motion, a step-and-shoot motion, or a modulated smooth motion with oscillatory velocity. The acquisition controller 114 of imaging system 110 may control the movement.

At block 306, a projection image of the object is acquired. Each projection image may be acquired by emitting penetrating particles from the source 104 toward a detector 106 with the object 102 positioned in between. The detector 106 detects the projection image responsive to the emitted penetrating particles that strike the detector surface of the detector 106. The acquisition controller 114 may control acquisition by instructing the source 104 to emit penetrating particles and instructing the detector 106 to capture an image.

If a series of images are being acquired, processing proceeds at step 302, with steps 302-306 repeated until the complete series of projection images is acquired. For example, if nine projection images are to be acquired, steps 302-306 may be performed nine times.

At block 308, a tomographic volume capable of exhibiting super-resolution is constructed from data representing the acquired series of projection images taking the scan path and the variable magnification of the detected penetrating particles into consideration. An imaging system 110, e.g., an image controller 116 may construct the tomographic volume based on data representing the projection images acquired by the detector 106.

Movement of the source 104 relative to the object 102 and the detector 106 results in features within the object 102 being projected onto different positions on the detection surface of the detector 106 in the scan path. The shift in position along the scan path, e.g., lateral to the chest wall, enables super-resolution in the scan path. By changing the distance between the source 104 and the detector 106, thereby varying the magnification of the detected penetrating particles, isotropic super-resolution may be obtained. In one embodiment, super-resolution is obtained without offsetting or shifting the detector 106 with respect to the source 104 in the x-direction or y-direction by moving the detector 106 or source 104 in said directions.

At block 310, super-resolution images are generated from the constructed tomographic volume. The reconstruction grid should have smaller pixels than the detector 106 in order to achieve super-resolution. The imaging controller 116 of the imaging system 110 may generate super-resolution images under the control of an operator. Additional details regarding generation of super-resolution images are found below and in U.S. Pat. No. 8,233,690 to Ng et al., titled Dynamic Tomographic Image Reconstruction and Rendering On-Demand, which is incorporated fully herein by reference.

The inventors recognized that due to the motion of the source 104 along a scan path relative to the object 102 and the surface of the detector 106, there are shifts in the features of the object 102 along the scan path, allowing for super-resolution along this direction. Moreover, the inventors recognized that to achieve sub-pixel sampling gain along a secondary direction (e.g., the y-direction), the detector 106 may be translated along the y-direction. The secondary motion promotes shifts in the image of an object 102 along the y-direction with each projection, which may enable super-resolution with respect to the motion in the y-direction. In one embodiment, a system that varies the source 104 and/or the detector 106 along the y-direction provides improved results for imaging objects that have a conical shape, substantially conical shape, or the like.

The inventors discovered that by reducing the angular spacing between the projections of the particles from the source 104 and/or by increasing the number of projections, the number of anisotropies in the images may be reduced. Thus, the range of positions over which super-resolution imaging in achieved may be increased. However, reducing the angular spacing between projections or increasing the total number of projections may be limited by increased costs and reduced efficiencies. Moreover, reducing the angular spacing or increasing the total number of projections does not provide super-resolution everywhere in the reconstructed volume.

Systems 100 with detector motion along the y direction advantageously increase the number of points with super-resolution if frequency is oriented along the y direction. However, the tissue coverage at the chest wall is increasingly reduced as the detector is translated anteriorly along the +y direction. Embodiments of systems 100 with the detector motion along the z direction offers the advantage of increased points with super-resolution and do not have the reduced tissue coverage, which is an additional advantage.

Surprisingly, the inventors discovered that super-resolution may be obtained over the entire reconstructed volume by varying the magnification of the projected image of the object as detected by the detector 106. The effect of varying the position of detector 106 along the z-direction as a function of the acquisition angle is to vary the magnification of the projected images as a function of the acquisition angle. For example, moving the detector 106 or the source 104 in the z-direction to change a distance between the source 104 and the detector 106 as the source 104 is positioned along the scan path varies the magnification of the projected images to achieve super-resolution over the entire reconstructed volume. In one embodiment, by varying the distance (e.g., along the z-direction) between the source 104 and the detector 106, super-resolution is achieved over the entire reconstructed volume. To vary the distance along the z-direction between the source 104 and the detector 106, the source 104 may be moved in the z-direction with respect to the detector 106 and/or the detector 106 may be moved in the z-direction with respect to the source 104. Additionally and/or alternatively, the source 104 and the detector 106 may be moved in the z-direction at a similar rate, such that the distance between the source 104 and the detector 106 is the same at each imaging position, but the distance between the object and the source and detector varies.

The inventors further discovered that moving the source 104 or detector 106 in the z-direction may be performed to optimize and/or maximize the amount of tissue scanned at each position (further discussed in Example 2). As referred to herein, the z-direction is defined with respect to a plane defined by the detector, such as a surface of the detector. For example, the z-direction may be a direction that extends perpendicular to the plane defined by the surface of the detector. In one embodiment for breast imaging, to optimize the tissue coverage at the chest wall, the detector 106 is elevated/moved toward the breast support when the source 104 is positioned farthest from the chest wall. Preferably, the detector 106 is elevated/moved as close as possible to the breast support when the source 104 is positioned farthest from the chest wall. Additionally and/or alternatively, the imaging system may vary the detector 106 with respect to the source 104 in both the y-direction and the z-direction.

Moreover, the inventors discovered that the positioning of the detector 106 to change the distance between the source 104 and the detector 106 may achieve super-resolution while avoiding excessive or problematic focal spot unsharpness. These results are surprising because in radiography one normally attempts to minimize the distance between the object 102 and the detector 106 to avoid focal spot unsharpness. However, the inventors discovered that by changing the distance between the source 104 and the detector 106 by moving the detector 106 in the z-direction, e.g., a motion of about 50 mm, super-resolution may be achieved over the reconstructed volume while avoiding excessive or problematic focal spot unsharpness. It is preferred to specify to the range of motion as a fraction of the average distance between the source 104 and the detector, for example, if the average source 104 to detector 106 distance is 600 mm, then a 10% range of motion is 60 mm. As used herein, the term "about" refers to a range of motion that is less than 20% of the average distance between the source 104 and detector 106.

Figure 4:
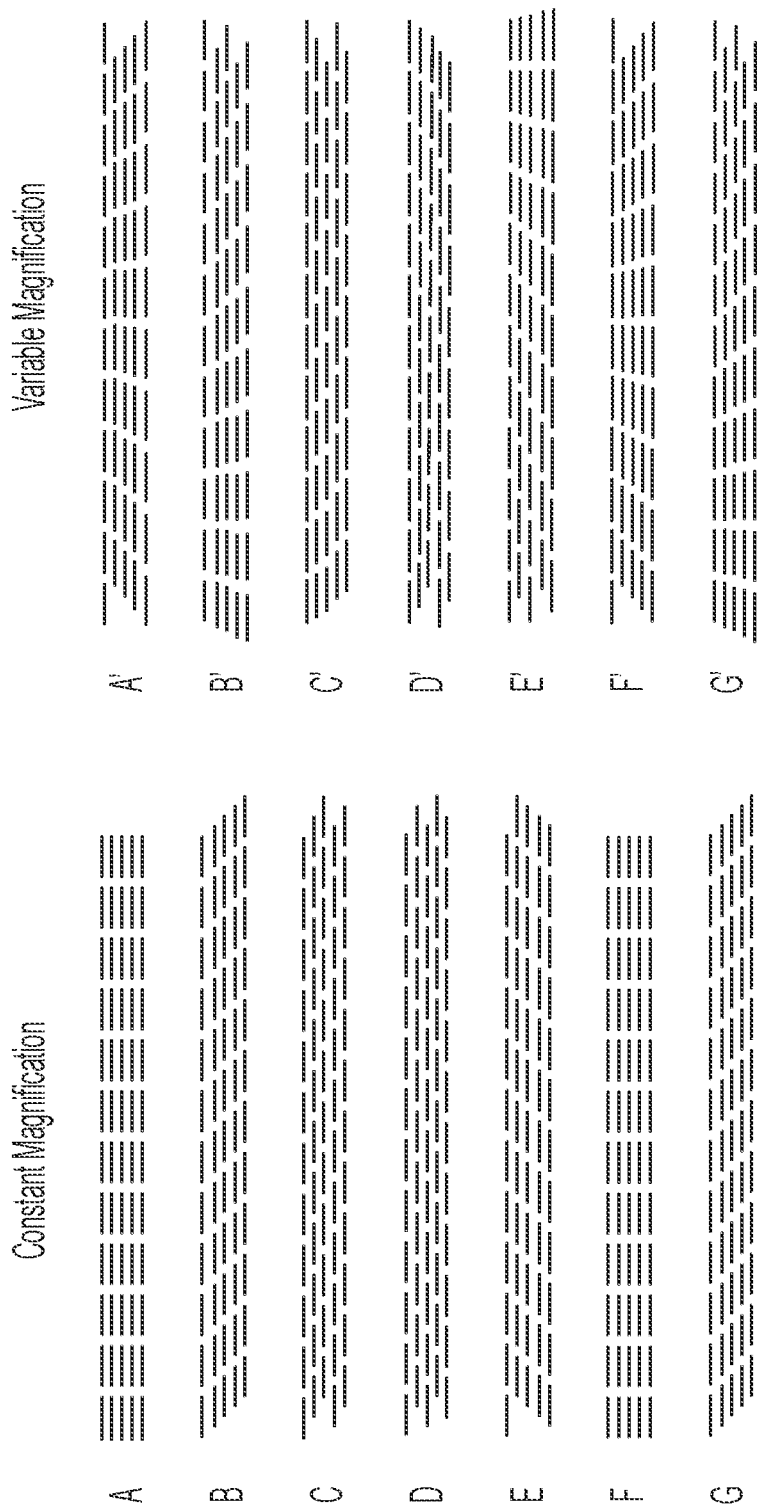
FIG. 4 is an illustration of backprojections of detector elements at various depths in the reconstruction for acquisition geometries with constant and variable magnification per projection in accordance with aspects of the invention.

For example, FIG. 4 illustrates projection images that are backprojected to various planes (A through G). In an acquisition with constant magnification in each projection image, there are certain planes (A and F) where the pixels from the five projections align exactly. It is in these planes that super-resolution is lost. There are other planes (B, C, D, E, and G) where the individual pixels do not align and, thus, super-resolution is achieved because of the subpixel shifts. In the acquisition with variable magnification per projection, the z coordinate of the detector 106 is varied between projections. As can be seen, there are no planes were the pixels are perfectly superimposed and, thus, super-resolution is achieved everywhere throughout the reconstructed volume. For further optimizing super-resolution, the r-factor is preferably less than unity at as many positions as practically possible.

Additional details regarding aspects of the invention are set forth in the following Example. Other implementation information may be found in U.S. Provisional Application Ser. No. 61/669,459, U.S. Provisional Application Ser. No. 61/763,310, and U.S. patent application Ser. No. 14/413,279, which are incorporated herein by reference for all purposes.

Example 1

Figure 5:
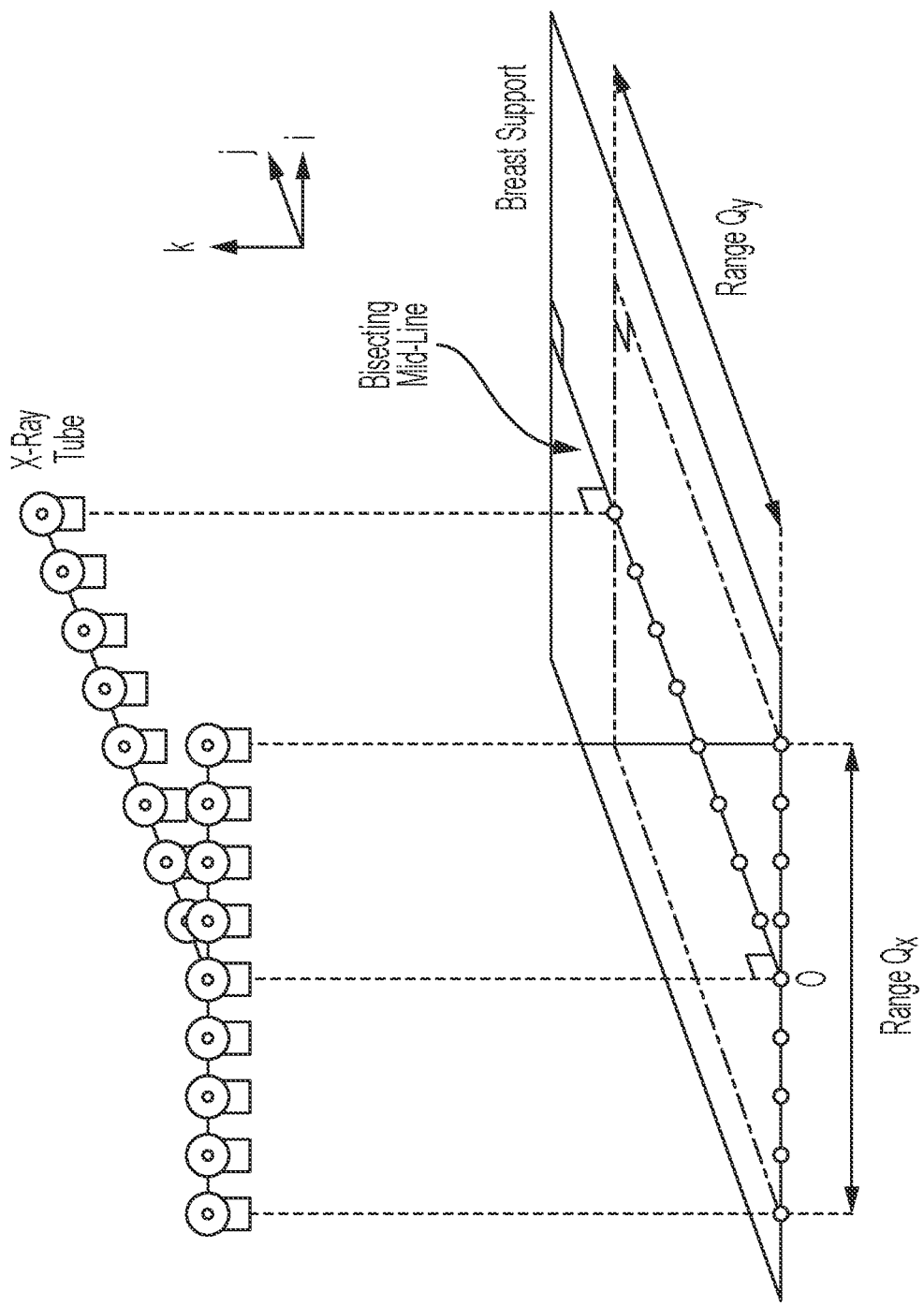
FIG. 5 is an illustration of a T-shaped x-ray tube trajectory according to an aspect of the invention.

Example 1 demonstrates an embodiment of a tomosynthesis system that includes movement of the focal spot along the posteroanterior (hereafter "PA") direction in a breast imaging application, which improves the modulation in the reconstruction of a Defrise phantom (e.g., as illustrated in FIG. 19 using a prototype tomosynthesis system that was constructed for research use at the University of Pennsylvania). One example of a trajectory following this design is shown in FIG. 5. The x-ray tube motion is "T-shaped", with projections along the x direction as well as the bisecting mid-line. The projections are acquired along the x direction over the extent $Q_x$ (i.e., $1 \leq n \leq N_x$), and the projections are acquired along the y direction over the extent $Q_y$ (i.e., $1+N_x \leq n \leq N_t$).

$$\overrightarrow{OA} = x_{FS}i + y_{FS}j + z_{FS}k, \quad (1)$$

$$x_{FS} = \begin{cases} \dfrac{(2n - N_x - 1)Q_x}{2(N_x - 1)}, & 1 \leq n \leq N_x \\ 0, & 1 + N_x \leq n \leq N_t \end{cases} \quad (2)$$

$$y_{FS} = \begin{cases} 0, & 1 \leq n \leq N_x \\ \dfrac{(n - N_x)Q_y}{N_t - N_x}, & 1 + N_x \leq n \leq N_t \end{cases} \quad (3)$$

The spacing between projections is thus $Q_x/(N_x-1)$ along the x direction and $Q_y/(N_t-N_x)$ along the perpendicular direction (PA). Since the two line segments that form the "T" have an intersection point, it follows that $$N_t = N_x + N_y - 1, \quad (4)$$

where $N_x$ is the number of projections along the x direction and $N_y$ is the number of projections along the bisecting mid-line.

Figure 8B:
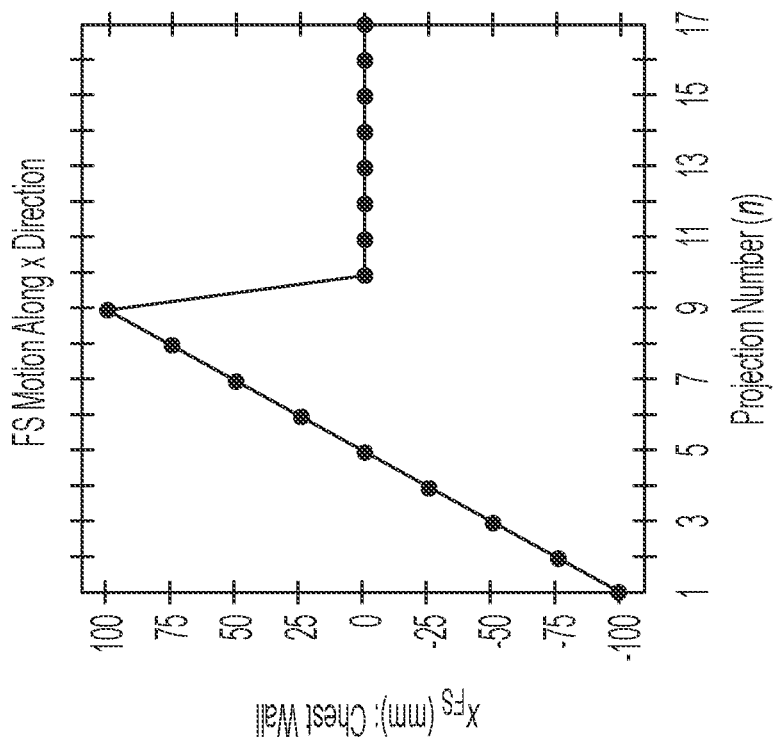
FIG. 8B is a graph of the x-coordinate of the focal spot plotted as a function of the projection number according to an embodiment of the invention.
Figure 8A:
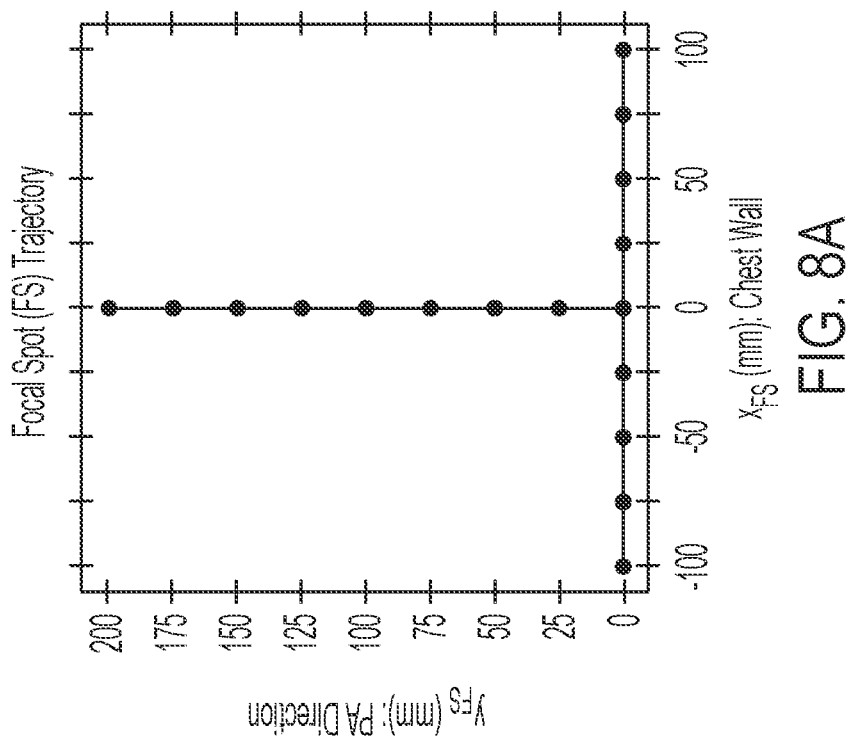
FIG. 8A is an illustration depicting a T-shaped x-ray tube trajectory in accordance with an embodiment of the invention.

FIG. 8A illustrates this trajectory in a DBT system with 17 projections, assuming that $N_x=N_y=9$ and that $Q_x=Q_y=200.0$ mm. In addition, FIG. 8B-8C show the x- and y-coordinates of the focal spot, respectively, as a function of the projection number (n).

Example 2

Figure 6:
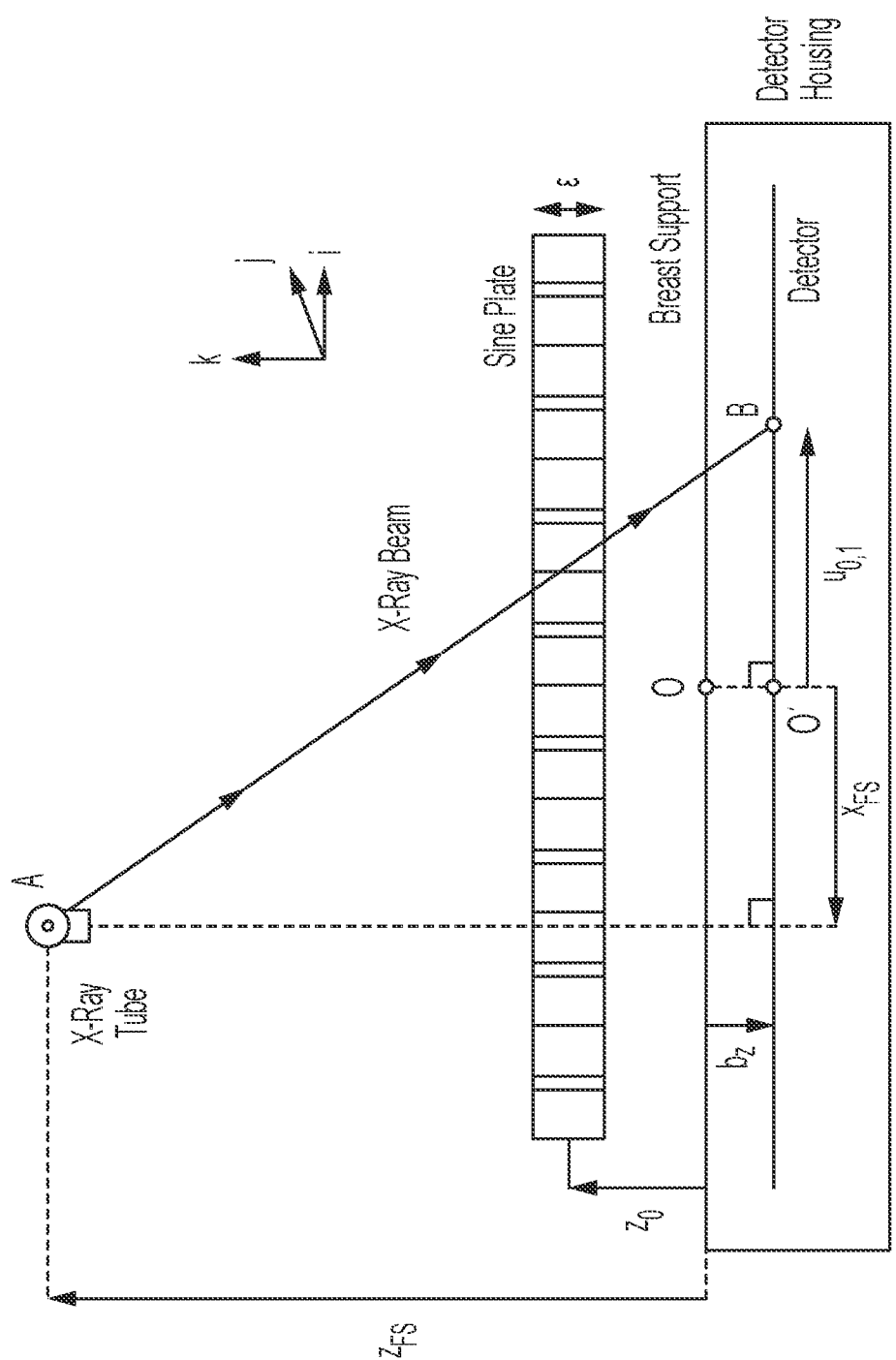
FIG. 6 is an illustration of the cross section of a sinusoidal test object in the plane of the chest wall in a breast imaging example in accordance with an aspect of the invention.
Figure 7:
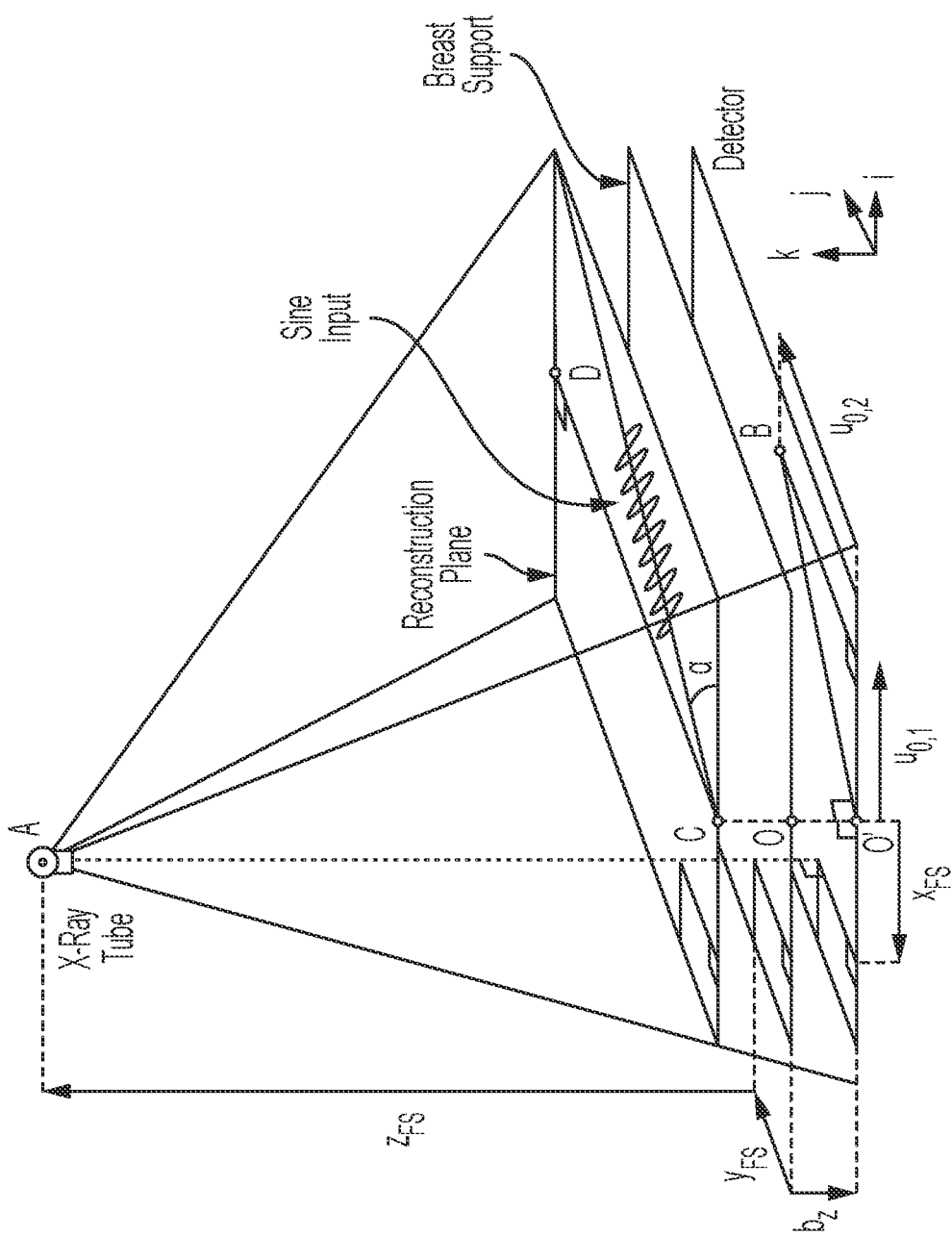
FIG. 7 is an illustration of the focal spot and an arbitrary detector position according to an aspect of the invention.

This Example provides modeling for an embodiment of tomosynthesis system that includes movement of the detector along the z direction as a technique for optimizing super-resolution. In FIGS. 6 and 7, a breast imaging example is considered such that the position of the detector relative to the breast support is denoted $b_z$. This displacement can be modeled by the vector $$\overrightarrow{OO'} = b_z K, \quad (5)$$

where O' denotes the primed origin (the midpoint of the chest wall side of the detector). For the purpose of this application, $b_z$ is taken to vary from $b_{z1}$ at the start of the scan (n=1) to $b_{z2}$ at the end of the scan (n=$N_t$). Also, $b_z$ may be assumed to be a linear function of the projection number, so that the increment of translation between each projection is $(b_{z2}-b_{z1})/(N_t-1)$.

$$b_z = b_{z1} + \frac{(b_{z2} - b_{z1})(n-1)}{N_t - 1} \quad (6)$$

Figure 8D:
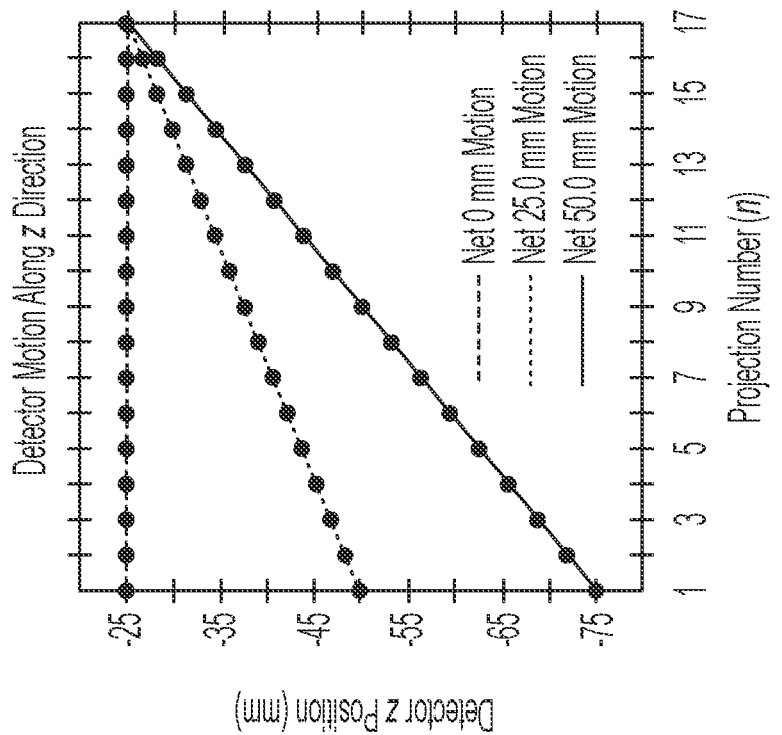
FIG. 8D is a graph depicting three detector trajectories plotted as a function of the projection number according to an aspect of the invention.
Figure 8C:
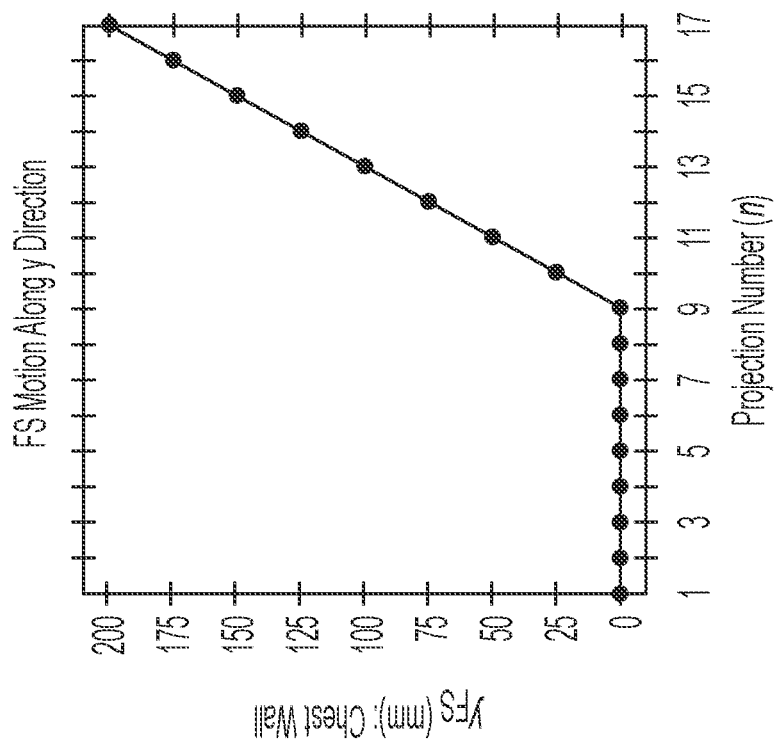
FIG. 8C is a graph depicting the focal spot in the plane of the chest wall for the first nine projections and increasingly displaced anterior to the chest wall in the remaining projections in accordance with an aspect of the invention.
Figure 9B:
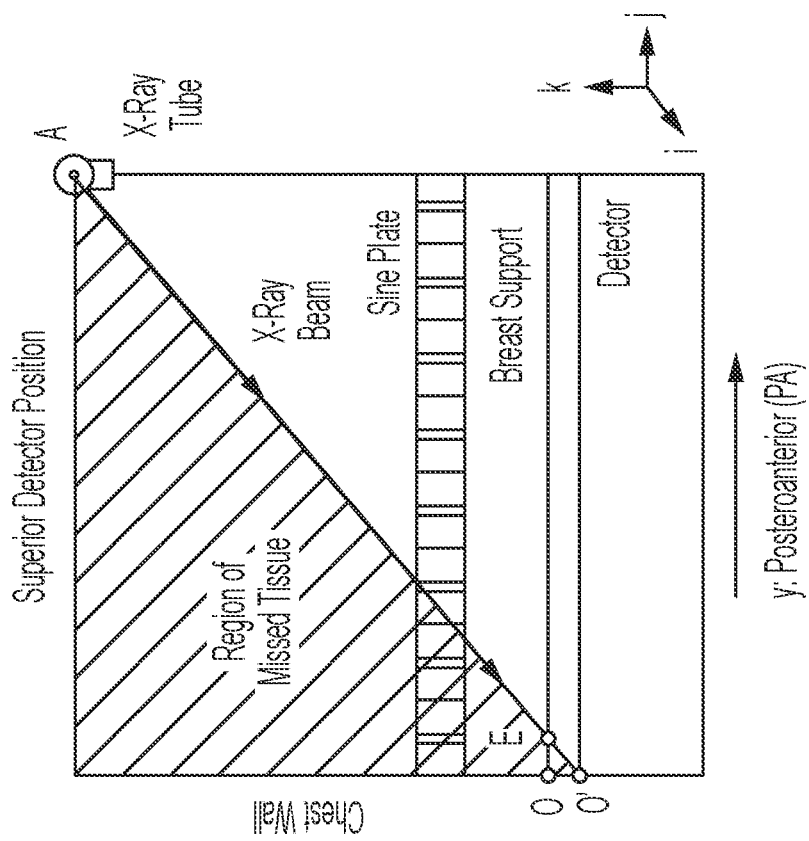
FIGS. 9A and 9B are illustrations of tissue coverage in two projection images in accordance with an aspect of the invention.
Figure 9A:
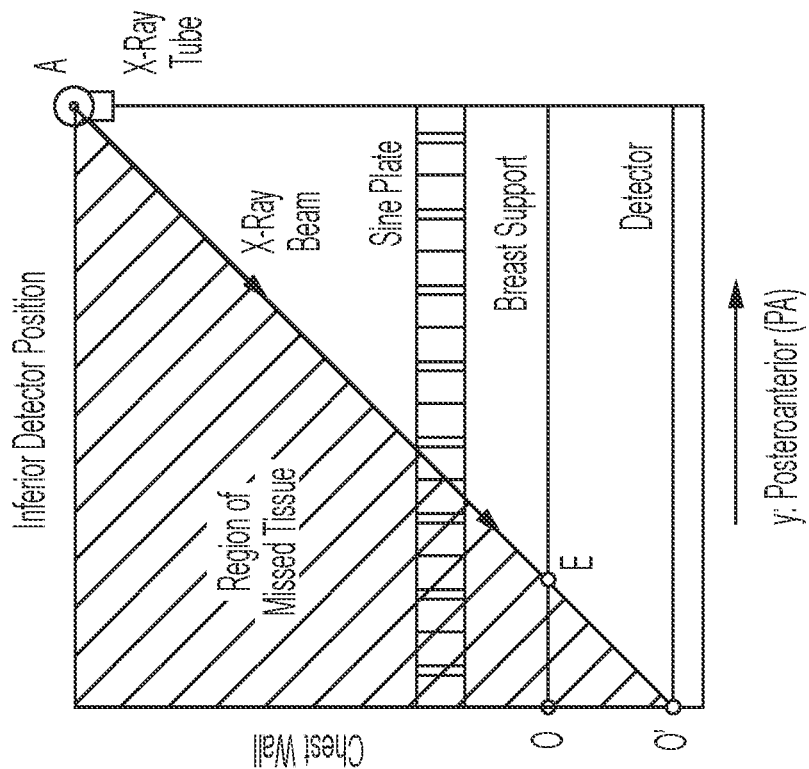

An example of this trajectory is shown in FIG. 8D, assuming that $N_t=17$ and $b_{z2}=-25.0$ mm. To vary the extent of the motion, three different values of $b_{z1}$ are considered; namely, −75.0, −50.0, and −25.0 mm. These three values of $b_{z1}$ correspond to net motions of 50.0, 25.0, and 0.0 mm, respectively. In FIG. 8D, the detector moves closer to the x-ray source with each successive projection, as illustrated by the fact that the trajectory is an increasing function. In a cranial-caudal (CC) view for a breast imaging application, this trajectory is inferior-to-superior. FIGS. 9A and 9B illustrate the advantage to using an ascending motion as opposed to a descending motion based on the focal spot positions. In FIGS. 9A and 9B, a ray is drawn between the point O' and a focal spot position anterior to the chest wall. This focal spot position corresponds to a point in the bisecting mid-line of the trajectory shown in FIG. 5. There is no signal detected for points to the left of line segment $\overline{AE}$ in FIGS. 9A and 9B. Consequently, there is a loss of tissue coverage at the chest wall due to the PA source motion. FIGS. 9A and 9B illustrate that one way to optimize and/or maximize the tissue coverage is to elevate the detector closer to the focal spot. As a result, the detector is preferably elevated as close as possible to the breast support. Since the focal spot is translated further away from the chest wall with each increasing projection (see, e.g., FIG. 8C), the tissue coverage can be maximized by ascending the detector as opposed to descending the detector during the acquisition of the projections.

In FIG. 8D, there is a fixed increment of detector motion per projection. Though not shown explicitly, alternate trajectories can be considered in which there is a different increment of detector motion per projection. Also, while the detector trajectory of FIG. 8D is a monotonic function, non-monotonic trajectories can also be considered in accordance with an embodiment of the invention. In summary, FIG. 8D is merely an example of a detector trajectory in which there is motion along the z direction.

Using the equations described previously, a position vector is now calculated from the focal spot at A to an arbitrary detector coordinate $(u_{0,1}, u_{0,2})$ at point B. Since $$\overrightarrow{O'B} = u_{0,1} i + u_{0,2} j, \quad (7)$$

it follows that $$\overrightarrow{AB} = \overrightarrow{AO} + \overrightarrow{OO'} + \overrightarrow{O'B} \quad (8)$$

$$= -\overrightarrow{OA} + \overrightarrow{OO'} + \overrightarrow{O'B} \quad (9)$$

$$= \xi_1 i + \xi_2 j + \xi_3 k, \quad (10)$$

where $$\xi_1 = u_{0,1} - x_{FS} \quad (11)$$

$$\xi_2 = u_{0,2} - y_{FS} \quad (12)$$

$$\xi_3 = b_z - z_{FS}. \quad (13)$$

This calculation of the vector $\overrightarrow{AB}$ may be used to determine the line integral of the ray through the object, and thus to calculate the signal for each projection image.

The line integral through the test object can be determined based on the equation of the ray from the focal spot at A to the detector at B.

$$\begin{pmatrix} x \\ y \\ z \end{pmatrix} = w \begin{pmatrix} \xi_1 \\ \xi_2 \\ \xi_3 \end{pmatrix} + \begin{pmatrix} x_{FS} \\ y_{FS} \\ z_{FS} \end{pmatrix} \quad (14)$$

In Eq. (14), w is a free parameter ranging from zero at point A to unity at point B. The values of z at the entrance ("entr") and exit surfaces of the test object are $z_0+\varepsilon/2$ and $z_0-\varepsilon/2$, respectively, where s is the thickness of the test object as shown in FIG. 6. Using Eq. (14), it can be shown that the values of w at these two surfaces are $$w_{entr} = \frac{z_0 + \varepsilon/2 - z_{FS}}{\xi_3} \quad (15)$$

$$w_{exit} = \frac{z_0 + \varepsilon/2 - z_{FS}}{\xi_3}. \quad (16)$$

The line integral of this ray along the path length ($\mathcal{L}$) through the object is thus $$\mathcal{A}_{\mu_{obj}} = \int_{\mathcal{L}} \mu_{obj} \cdot ds, \quad (17)$$

where the attenuation coefficient ($\mu_{obj}$) is taken to vary sinusoidally along the polar angle α (FIG. 7) with frequency $f_0$ $$\mu_{obj} = C_{obj} \cdot \cos(2\pi f_0[(x-x_0)\cos\alpha + (y-y_0)\sin\alpha]) \cdot \text{rect}\left(\frac{z-z_0}{\varepsilon}\right), \quad (18)$$

and where the differential length (ds) along the ray is given by the expression $$ds = \sqrt{\left(\frac{dx}{dw}\right)^2 + \left(\frac{dy}{dw}\right)^2 + \left(\frac{dz}{dw}\right)^2}\, dw \quad (19)$$

$$= \sqrt{\xi_1^2 + \xi_2^2 + \xi_3^2}\, dw. \quad (20)$$

In this example, the cosine function attains the amplitude $C_{obj}$ at the x- and y-coordinates of $x_0$ and $y_0$, respectively. The line integral simplifies as follows:

$$\mathcal{A}\mu_{obj} = \kappa_1 \cdot \int_{w_{entr}}^{w_{exit}} \cos[2\pi f_0(\xi_1\cos\alpha + \xi_2\sin\alpha)w + \kappa_2]\, dw \quad (21)$$

$$= \frac{\kappa_1 \cdot (\sin[2\pi f_0(\xi_1\cos\alpha + \xi_2\sin\alpha)w_{exit} + \kappa_2] - \sin[2\pi f_0(\xi_1\cos\alpha + \xi_2\sin\alpha)w_{entr} + \kappa_2])}{2\pi f_0(\xi_1\cos\alpha + \xi_2\sin\alpha)}, \quad (22)$$

where $$\kappa_1 = C_{obj}\sqrt{\xi_1^2 + \xi_2^2 + \xi_3^2} \quad (23)$$

$$\kappa_2 = 2\pi f_0[(x_{FS}-x_0)\cos\alpha + (y_{FS}-y_0)\sin\alpha]. \quad (24)$$

By using a sum-to-product trigonometric identity, it can be shown that Eq. (22) can be simplified further.

$$\mathcal{A}\mu_{obj} = \frac{-\varepsilon\kappa_1}{\xi_3} \cdot \cos\left[\frac{2\pi f_0}{\xi_3}(\xi_1\cos\alpha + \xi_2\sin\alpha)(z_0 - z_{FS}) + \kappa_2\right] \cdot \text{sinc}\left[\frac{\varepsilon f_0}{\xi_3}(\xi_1\cos\alpha + \xi_2\sin\alpha)\right] \quad (25)$$

This expression can in turn be used to calculate the signal in each detector element (del). The centroid of each del may be given by the coordinate $(m_x a_x,(m_y+1/2)a_y)$, where $a_x$ and $a_y$ are the del dimensions along the two respective directions and where $m_x$ and $m_y$ are integer indices. While $m_x$ can be any integer, $m_y$ must be non-negative, since signal is not recorded posterior to the chest wall (e.g., FIGS. 9A and 9B). Assuming that each del is uniformly sensitive to x rays, the signal recorded by the $m^{th}$ del is thus $$\mathcal{D}\mu_{obj}(m_x, m_y) = \int_{a_y m_y}^{a_y(m_y+1)} \int_{a_x(m_x-1/2)}^{a_x(m_x+1/2)} \mathcal{A}\mu_{obj}\, \frac{du_{0,1}}{a_x}\, \frac{du_{0,2}}{a_y} \quad (26)$$

$$= \lim_{J_{del,2}\to\infty} \frac{1}{J_{del,2}} \sum_{j_{del,2}=1}^{J_{del,2}} \left[\lim_{J_{del,1}\to\infty} \frac{1}{J_{del,1}} \sum_{j_{del,1}=1}^{J_{del,1}} \mathcal{A}\mu_{obj}\bigg|_{u_{0,1}=a_x\left(\frac{j_{del,1}-1/2}{J_{del,1}}+m_x-\frac{1}{2}\right)}\right]\bigg|_{u_{0,2}=a_y\left(\frac{j_{del,2}-1/2}{J_{del,2}}+m_y\right)} \quad (27)$$

Eq. (27) illustrates how a middle sum can be used to evaluate this double integral.

Based on the signal recorded for each projection, the reconstruction may be calculated using simple backprojection (hereafter "SBP"). To determine the SBP reconstruction at the point (x, y, z), it is first necessary to identify the del that is intercepted by the ray between the points $(x_{FS}, y_{FS},$ $z_{FS})$ and (x, y, z). It can be shown that this ray strikes the detector position with coordinates $$u_{1,SBP} = \frac{x(b_z - z_{FS}) + zx_{FS} - b_z x_{FS}}{z - z_{FS}} \quad (28)$$

$$u_{2,SBP} = \frac{y(b_z - z_{FS}) + zy_{FS} - b_z y_{FS}}{z - z_{FS}}. \quad (29)$$

Eqs. (28)-(29) can be derived using a computer algebra system (e.g., Maple 16, Maplesoft, Waterloo, Ontario) to solve Eqs. (11)-(14) for $u_1$ and $u_2$. This detector position corresponds to the del with indices $$m_{x,SBP} = \left\lfloor \frac{u_{1,SBP} + a_x/2}{a_x} \right\rfloor \quad (30)$$

$$m_{y,SBP} = \left\lfloor \frac{u_{2,SBP}}{a_y} \right\rfloor, \quad (31)$$

where $\lfloor\ \rfloor$ denotes the floor function, which is defined as follows.

$$\lfloor v_1 \rfloor = \max\{v_2 \in \mathbb{Z} : v_2 \leq v_1\} \quad (32)$$

Averaging the backprojected signal for all projections at the point (x, y, z) yields the SBP reconstruction.

$$\mu_{SBP} = \frac{1}{N_t} \cdot \sum_n \mathcal{D}\mu_{obj}(m_{x,SBP}, m_{y,SBP}) \quad (33)$$

This formula assumes that the reconstruction is prepared on an infinitesimally fine (i.e., non-pixelated) grid. To measure signal along the polar angle α (the direction of the input frequency), $$\begin{pmatrix} x \\ y \\ z \end{pmatrix} = \begin{pmatrix} x_0 \\ y_0 \\ z_0 \end{pmatrix} + \begin{pmatrix} \cos\alpha & -\sin\alpha & 0 \\ \sin\alpha & \cos\alpha & 0 \\ 0 & 0 & 1 \end{pmatrix}\begin{pmatrix} x'' \\ y'' \\ z'' \end{pmatrix}, \quad (34)$$

Eq. (34) can be used to evaluate the reconstruction along the x" direction.

To determine whether the high-frequency test object is resolved in the reconstruction, the one-dimensional (1D) Fourier transform of $\mu_{SBP}$ may be calculated. While the Fourier transform is usually calculated with infinite integration limits, it is useful to calculate the integral over a finite interval in order to quantify super-resolution locally, and thus to determine anisotropies that vary with position. As shown below, a middle sum can be used to evaluate this integral $$\mathcal{F}_1 \mu_{SBP} \approx \int_{x''_{min}}^{x''_{max}} \mu_{SBP} e^{-2\pi i f''_x x''} dx'' \quad (35)$$

$$= \lim_{J_{FT} \to \infty} \left( \frac{x''_{max} - x''_{min}}{J_{FT}} \right) \sum_{J_{FT}=1}^{J_{FT}} \mu_{SBP} e^{-2\pi i f''_x x''} \bigg|_{x''=x''_{min}+(x''_{max}-x''_{min})\left(\frac{J_{FT}-1/2}{J_{FT}}\right)}, \quad (36)$$

where $x''_{min}$ and $x''_{max}$ are the integration limits. Assuming that the frequency is measured along the $x''$ direction, the Fourier transform should peak at the frequencies $f''_x = \pm f_0$ and should be zero elsewhere. The existence of a major peak at another frequency indicates that the input object is not properly resolved. For the purpose of this example, the limits of integration in Eq. (35) are chosen to be $-3.125$ mm and $+3.125$ mm. This interval corresponds to 50 cycles of a $8.0$ mm$^{-1}$ input frequency. This frequency is further discussed in Example 3 as an example of a frequency that exceeds the alias frequency of a detector with 0.085 mm pixelation.

Example 3

A conventional acquisition geometry was modeled using a DBT system having the following parameters: $z_{FS}=625.0$ mm, $Q_x=200.0$ mm, $b_{z1}=b_{z2}=-25.0$ mm, and $N_1=17$. It is assumed that the detector is the AXS-2430 (Analogic, St Laurent, Quèbec, Canada), for which $a_x=a_y=0.085$ mm. Since the detector elements (dels) are square, the del size can be abbreviated a in either direction. To quantify the existence of super-resolution, the frequency $8.0$ mm$^{-1}$ is chosen for simulation, since this frequency exceeds the detector alias frequency of $0.5 a^{-1}=5.88$ mm$^{-1}$.

In DBT, a calcification is typically 1.0 mm in diameter or less. Accordingly, it is assumed that the sine plate is thin ($\varepsilon=0.50$ mm). Also, in accordance with the present inventors' work, it is assumed that $C_{obj}=\varepsilon^{-1}=2.0$ mm$^{-1}$, so that the line integral through $\mu_{obj}$ is normalized at normal incidence. The SBP reconstruction is calculated in the plane corresponding to the mid-thickness of the sine plate (i.e., the depth $z=z_0$). In this plane, the centroid of this object is chosen to be the coordinate $(x_0, y_0)=(0, 40.0$ mm$)$. This coordinate corresponds to a point that is 40.0 mm anterior to the chest wall along line segment $\overline{CD}$ (the perpendicular bisector to the chest wall in a breast imaging application), as shown in FIG. 7.

The input frequency is assumed to be oriented along the tube travel direction (x). To evaluate the reconstruction along the polar angle aligned with the input frequency, Eq. (51) can be applied with the substitutions: $\alpha=0°$, $y''=0$, and $z''=0$. With this notation, the SBP reconstruction is plotted along the $x''$ direction, so that the position $x''=0$ corresponds to the centroid $(x_0, y_0, z_0)$.

Figures 10A, 10B:
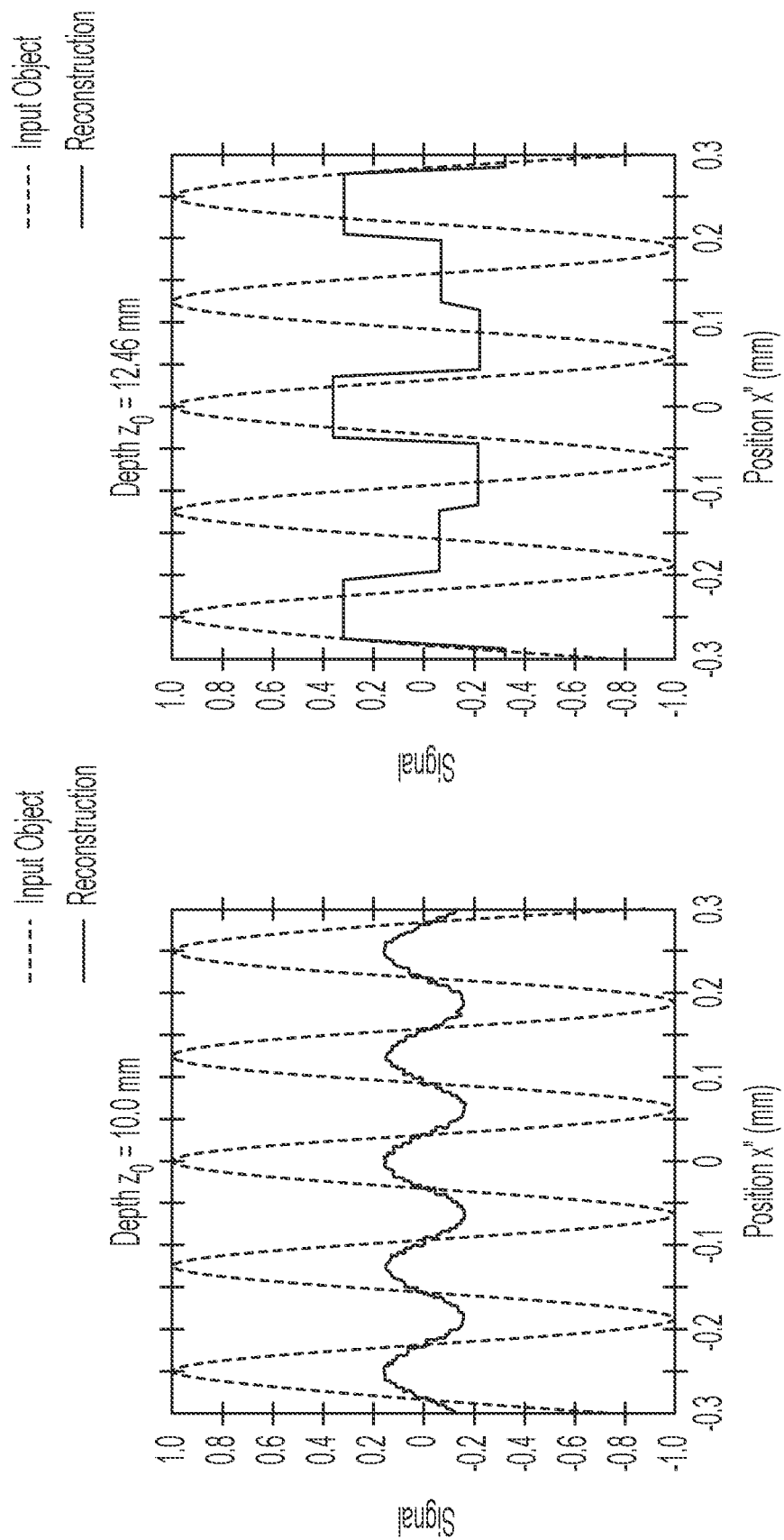
FIGS. 10A and 10B are graphs illustrating simulations of reconstructions of a sinusoidal test object at different depths in accordance with a conventional acquisition geometry for tomosynthesis.

FIGS. 10A-10D illustrate how super-resolution is dependent upon the depth $z_0$ above the breast support. While the sinusoidal input is resolved at the depth $z_0=10.0$ mm (as seen in FIG. 10A), the same object is aliased at the depth $z_0=12.5$ mm (as seen in FIG. 10B). The reconstruction in FIG. 10B is step-like, with the width of each step matching the del size (0.085 mm). The appearance of this reconstruction is similar to a single projection image. These two subplots illustrate how the intrinsic resolution of high-frequency content in the reconstruction varies with depth.

Figure 10D:
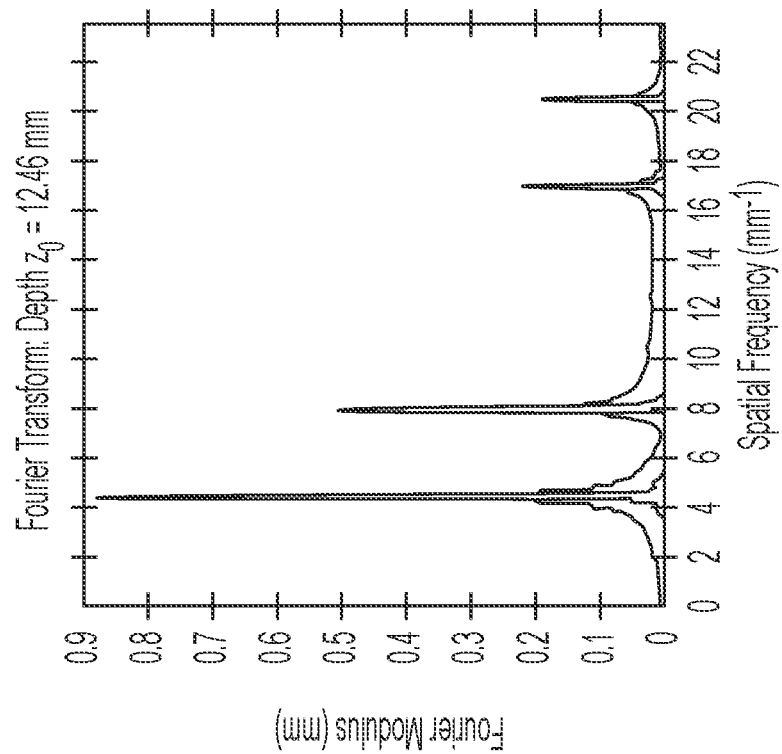
FIGS. 10C and 10D are graphs illustrating Fourier transforms of the respective reconstructions of FIGS. 10A and 10B.
Figure 10C:
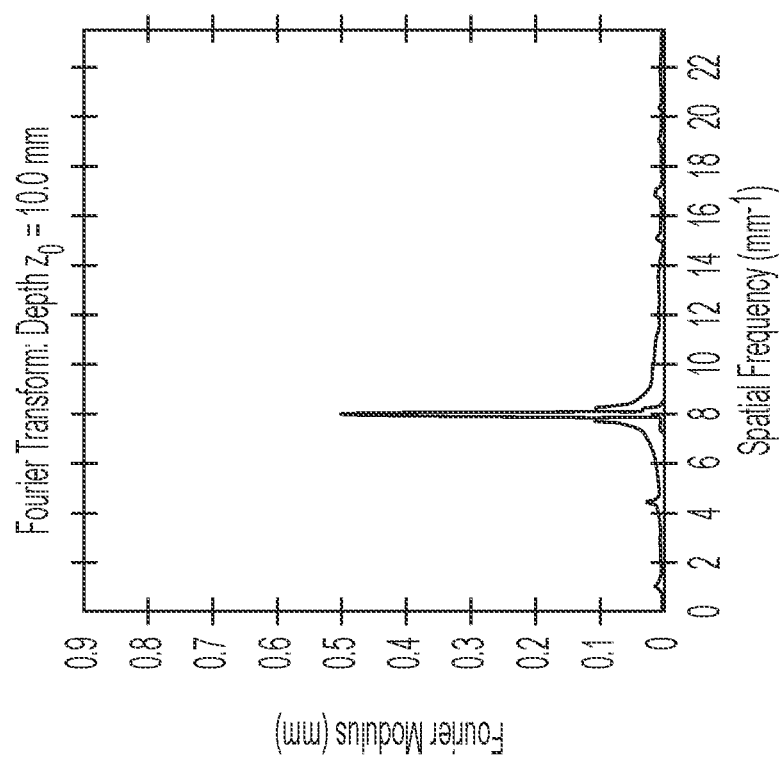
Figures 11E, 11F:
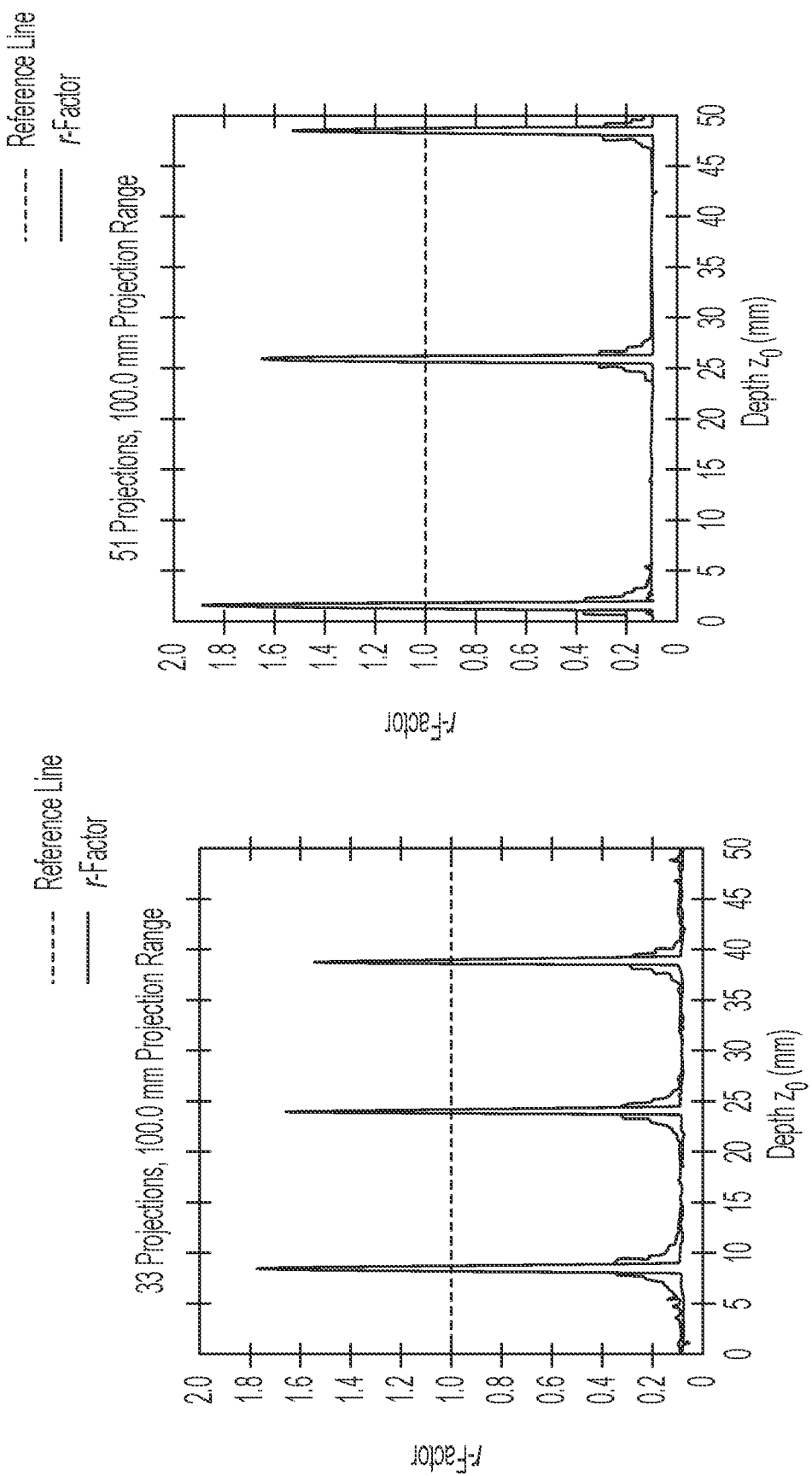

The 1D Fourier transforms of these reconstructions are calculated in FIGS. 10C and 10D. In order to achieve super-resolution, the frequency of the major peak should match the input frequency (e.g., $8.0$ mm$^{-1}$). This result is seen at the depth $z_0=10.0$ mm (FIG. 10C) but not at the depth $z_0=12.5$ mm (FIG. 10D). FIGS. 10A-10D illustrate that the feasibility of super-resolution is dependent on depth ($z_0$).

Using the Fourier transform, a metric termed the r-factor was calculated to quantify super-resolution in more detail. The r-factor is the ratio of the amplitude of the largest peak less than the alias frequency (e.g., $5.88$ mm$^{-1}$) to the amplitude at the input frequency. Super-resolution is achieved provided that $r<1$, but aliasing is present provided that $r \geq 1$. At the depth $z_0=10.0$ mm (FIG. 10C), the amplitude at the largest peak less than the alias frequency ($4.43$ mm$^{-1}$) is 0.0254 mm, while the amplitude at $8.0$ mm$^{-1}$ is 0.502 mm, yielding $r=0.0506$ and hence super-resolution. By contrast, at the depth $z_0=12.5$ mm (FIG. 10D), the amplitude of the major peak at $4.48$ mm$^{-1}$ is 0.877 mm, while the amplitude at $8.0$ mm$^{-1}$ is 0.504 mm, yielding $r=1.74$ and hence aliasing.

FIGS. 11A-11F quantify the anisotropies in super-resolution as a function of the depth $z_0$ using the r-factor. There are sharp peaks corresponding to multiple depths at which super-resolution cannot be achieved. FIGS. 11A-11F illustrate that the anisotropies are dependent upon the range of source motion ($Q_x$) and the number of projections ($N_t$). In an acquisition geometry with a 200.0 mm range of source motion and 17 projections, super-resolution cannot be achieved at 14 depths between 0 and 50.0 mm above the breast support. FIGS. 11A-11F demonstrates that one way to minimize the number of anisotropies is to increase the number of projections. Assuming a 200.0 mm range of source motion, there are seven sharp peaks if 33 projections are used, and there are five sharp peaks if 51 projections are used.

In addition, it is shown that the number of anisotropies can be minimized by reducing the range of source motion. For example, by changing the range of source motion from 200.0 mm to 100.0 mm, the number of sharp peaks is reduced from 14 to seven, assuming that there are 17 projections. In summary, the spacing between the anisotropies can be minimized either by increasing the number of projections or by reducing the range of source motion. These two approaches are similar in that they both reduce the spacing between the source positions in the acquisition of the projections.

Figure 12B:
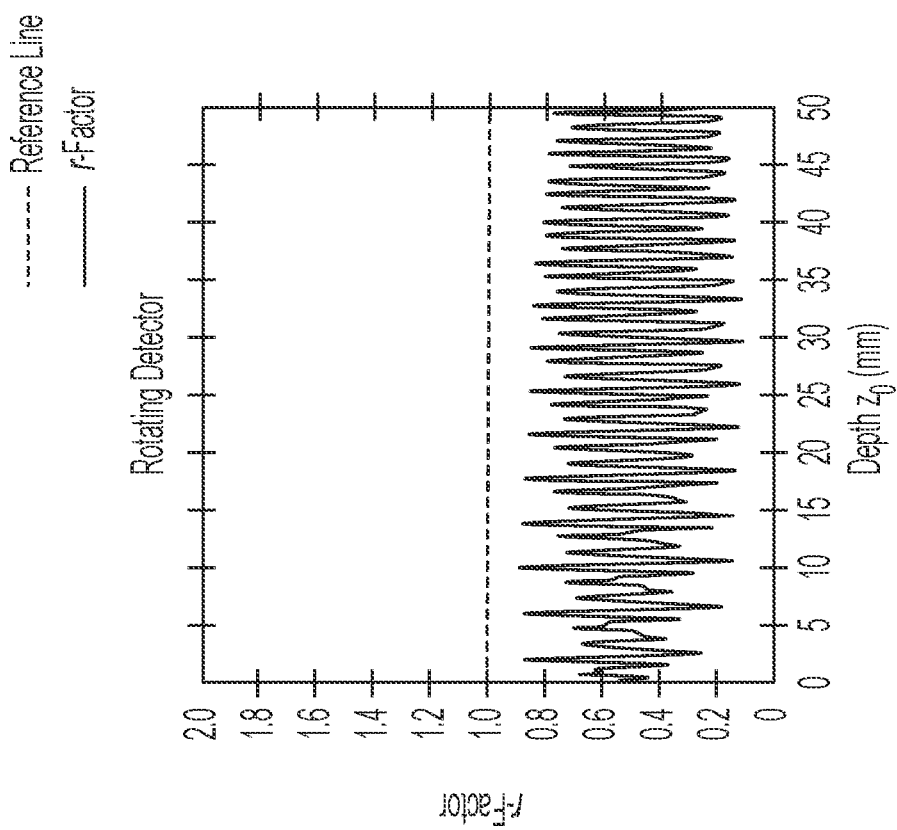
FIGS. 12A and 12B are graphs illustrating the r-factor as a function of depth for a stationary detector and a rotating detector respectively in accordance with a conventional acquisition geometry for tomosynthesis.
Figure 12A:
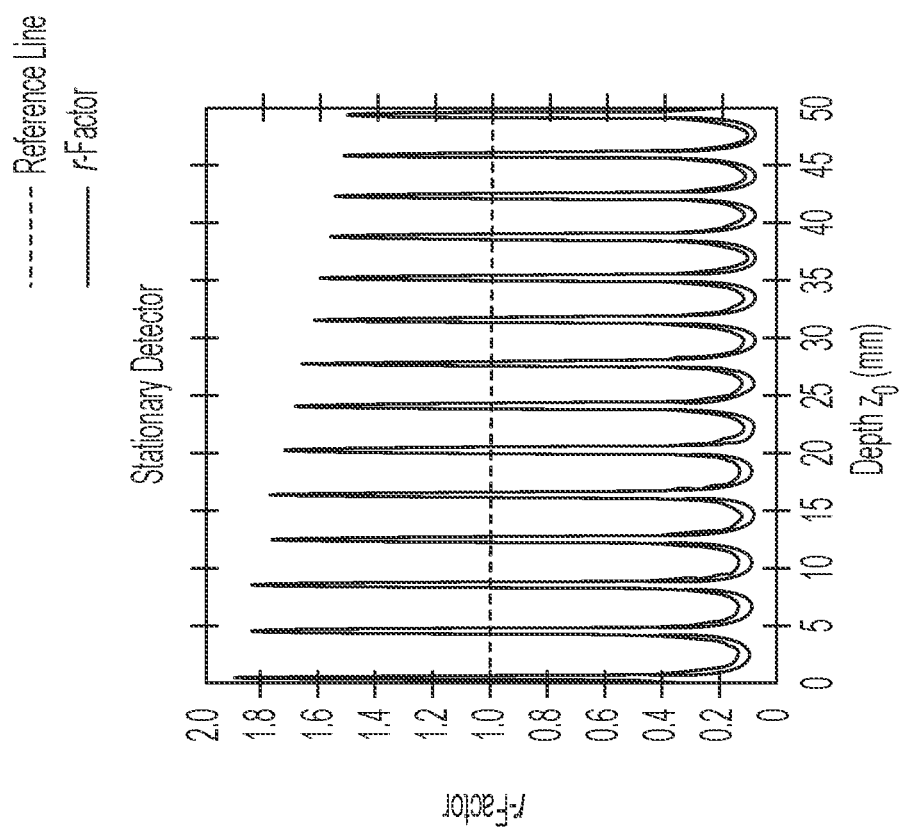

One of the assumptions made in FIGS. 11A-11F is that local measurements of the r-factor are centered on the coordinate $x_0=0$. For all possible values of $y_0$ and $z_0$, this coordinate is a point in the mid-line perpendicular to the chest wall (line segment $\overline{CD}$ in FIG. 7). FIGS. 12A and 12B investigates the consequence of shifting this coordinate laterally (namely, $x_0=-90.0$ mm), assuming that $y_0=40.0$ mm, $Q_x=200.0$ mm, and $N_1=17$.

In plotting the r-factor as a function of depth ($z_0$), FIGS. 12A and 12B demonstrates that the existence of sharp peaks depends on whether a stationary detector or a rotating detector is used. For example, in a system with a stationary detector (FIG. 12A), there may be 14 sharp peaks for which the r-factor exceeds unity. By contrast, in an example of a system with 0.50° of detector rotation per projection (FIG. 12B), the r-factor does not exceed unity at any depth. This result indicates that the use of detector rotation is a tool for minimizing anisotropies in super-resolution. FIG. 12B is prepared using equations which account for detector rotation.

In a traditional embodiment of a system with a rotating detector, there are sharp peaks in the r-factor for local measurements centered on the coordinate $x_0=0$. For this reason, detector rotation minimizes the anisotropies at points that are sufficiently lateral to line segment $\overline{CD}$ in FIG. 7.

Example 4

Figure 13:
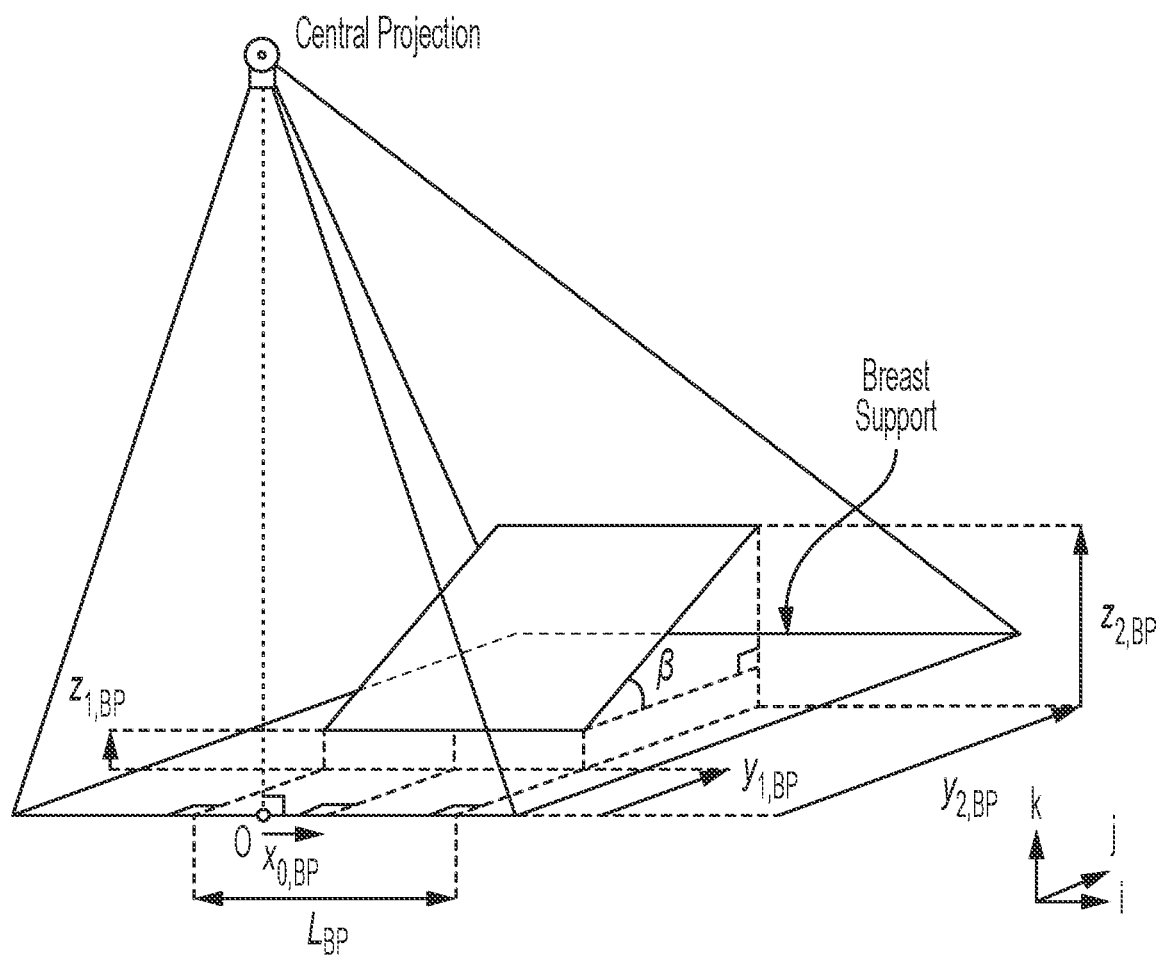
FIG. 13 is an illustration depicting a set up for acquiring a projection image of a bar pattern phantom in accordance with a conventional acquisition geometry for tomosynthesis.

This Example experimentally confirms the anisotropies by orienting the plane of a bar pattern (BP) phantom at an angle ($\beta$) relative to the breast support using a goniometry stand (FIG. 13). This approach allows the test frequency to be visualized over a continuous range of depths ($z_0$) in a single DBT acquisition. As shown in FIG. 13, the input frequency is aligned with the x direction, similar to Example 3, regardless of the specific value of $\beta$ that is used to angle the phantom.

Following the approach shown in FIG. 13, DBT images were acquired with a Selenia Dimensions system (Hologic Inc., Bedford, Mass.). The DBT acquisition was performed with a W/Al target-filter combination at 30 kVp and 25 mAs. The reconstruction was then calculated with the software Piccolo™ (available from Real Time Tomography, LLC of Villanova, Pa.). This software has a feature that allows the user to alter the angle of the reconstruction plane, so that it matches the oblique plane of the phantom.

FIGS. 14A and 14B illustrates the reconstruction of the frequency 5.0 line pairs per millimeter (lp/mm). This frequency exceeds the alias frequency (3.57 lp/mm) for a 0.140 mm detector. The reconstruction was performed with smaller pixelation than the detector (0.0215 mm), which is an important condition for achieving super-resolution. As such, the reconstruction was magnified by a factor of 6.51 relative to the detector.

In the first DBT acquisition (FIG. 14A), the middle line pair was roughly centered on the coordinate $x_{0,BP}=0$. To investigate whether there was an alignment imprecision, the reconstruction software was used to determine this value more exactly. It was found that $x_{0,BP}=-3.0$ mm. Additional parameters that can be determined with the reconstruction software are as follows: $\beta=47°$, $L_{BP}6.0$ mm, $y_{1,BP}57$ mm, $y_{2,BP}77$ mm, $z_{1,BP}=11$ mm, and $z_{2,BP}=32$ mm.

Figures 15A, 15B:
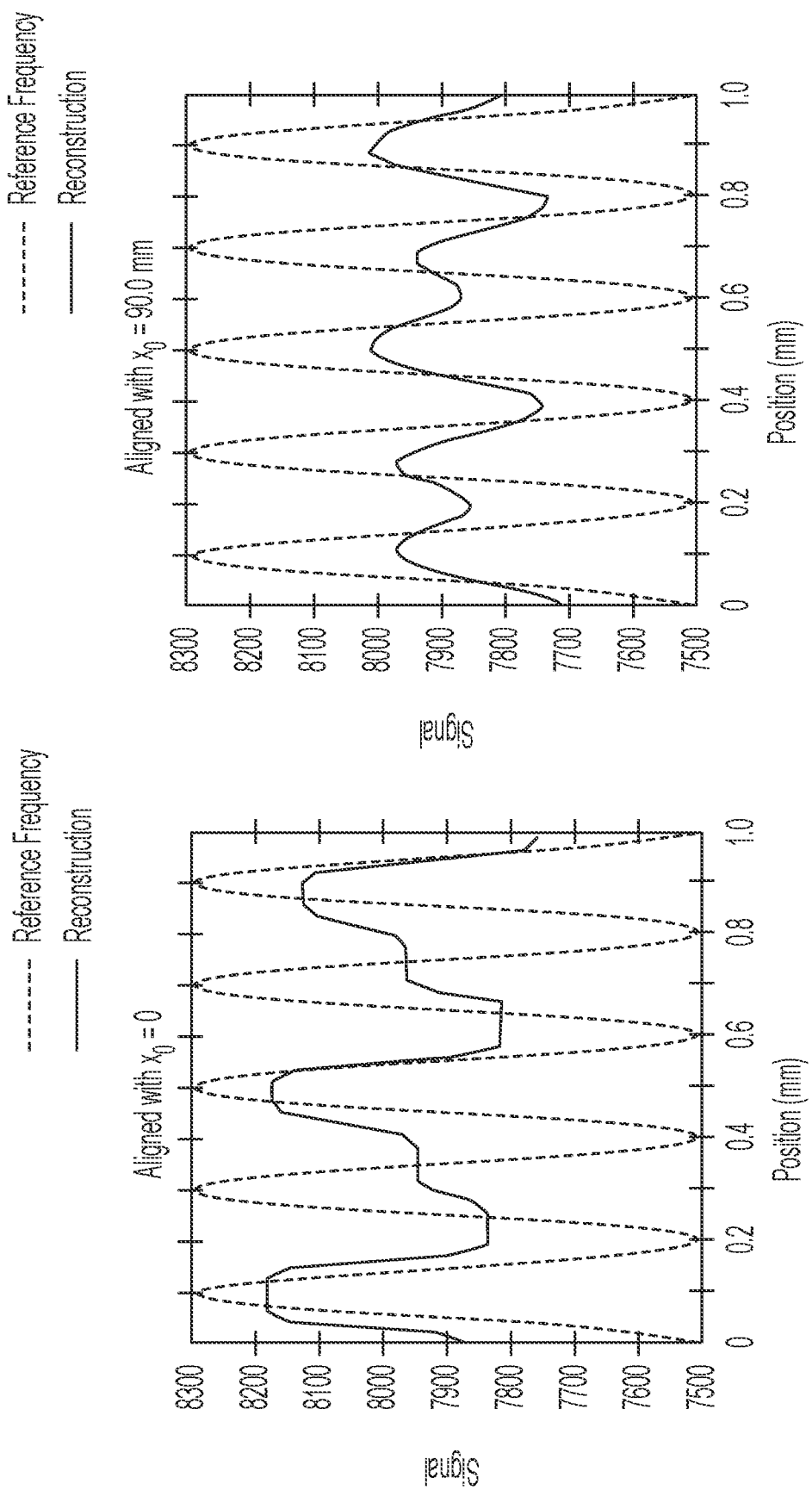
FIGS. 15A and 15B are graphs illustrating signal as a function of position in the respective reconstructions of FIGS. 14A and 14B.

FIG. 14A confirms the models discussed above by illustrating that super-resolution is not achievable at all depths ($z_0$). There are aliasing artifacts indicated by the arrows. FIG. 15A shows the signal through one artifact (the middle artifact out of the three). The peaks and troughs in this plot do not match those of the reference frequency (5.0 mm$^{-1}$), reflecting the presence of aliasing.

Using the reconstruction software, it was determined that there are 6.34 and 6.49 mm spacing between the centroids of adjacent aliasing artifacts in FIG. 14A. Based on calculations for a rotating detector, it can be shown that these spacings are predicted correctly to within absolute errors of 0.07 and 0.06 mm, respectively.

The phantom was then re-positioned with the middle line pair roughly centered on the coordinate $x_{0,BP}=-90.0$ mm as shown in FIG. 14B. The reconstruction software showed that our positioning of the phantom was accurate to within 1.3 mm; specifically, $x_{0,BP}=-88.7$ mm. The software also demonstrated that the values of $\beta$, $L_{BP}$, $y_{1,BP}$, and $y_{2,BP}$ were identical to the ones described in the above examples. However, there was a slight difference in the positioning of the z coordinates of the phantom, since $z_{1,BP}=8$ mm and $z_{2,BP}=29$ mm.

FIG. 15B illustrates the plot profile of this reconstruction. The plot profile was created at the same z-coordinate as the middle aliasing artifact in FIG. 14A. Although there is some variation in the signal at each peak and trough, the positions of each peak and trough match the reference frequency, indicating that the test object is resolved. As one would expect from the model, FIG. 14B indicates that there are no aliasing artifacts at any depth.

The quality of super-resolution that is achieved in FIG. 14B is clearly different from that of FIG. 14A. There is sharper, higher-quality super-resolution in FIG. 14A, e.g., at the regions to the left and right of the arrows. The simulations in previous examples demonstrate that the quality of super-resolution can be modeled by the r-factor. The r-factor should be as close to zero as possible to achieve high-quality super-resolution. The relatively poor-quality super-resolution that is seen in FIG. 14B is to be expected based on the results shown in FIG. 12B.

Example 5

The results presented in Examples 3 and 4 indicate that there is variation in the quality of super-resolution throughout the 3D image. One way to quantify this variation is to determine the r-factor at every point in a volume-of-interest (VOI), and calculate a histogram. An alternate approach is to calculate the histogram by randomly sampling 500 points in the VOI, which is depicted in FIG. 16A for a breast imaging example. For the purpose of FIG. 16A, the VOI is a rectangular prism with dimensions 200.0×100.0×50.0 (in mm) and 0.050 mm spacing between points in each direction. The VOI is centered on the point (0, 55.0, 25.0) (in mm).

In Example 2, it was noted that the Fourier transform of $\mu_{SBP}$ is evaluated over an interval that is 6.25 mm wide. Considering the frequency along a 90° polar angle, this interval could include positions posterior to the chest wall, for which there is no signal recorded by the detector (FIGS. 9A-9B). As a result, the r-factor is not well-defined if the y-coordinate of the point-of-interest is less than 3.125 mm. A VOI was chosen for which the y-coordinate of each point is 5.0 mm or higher. This approach is designed to ensure that the reconstruction is well-defined over the interval used to calculate the Fourier transform.

FIG. 16 A illustrates the histogram for a conventional acquisition geometry, assuming that $f_0=8.0$ mm$^{-1}$, $\alpha=0°$, $\varepsilon=0.50$ mm, $Q_x200.0$ mm, and $N_t=17$. This system is similar to the one simulated in Example 3, for which there is linear source motion and a stationary detector. It was confirmed that super-resolution cannot be achieved at all points in the VOI. The r-factor exceeded unity at 45 points out of 500. Hence, there is aliasing at 9.0% of the points in the VOI.

To determine whether re-designing the detector motion yields an improvement in image quality, cumulative histograms of the r-factor were calculated for the three detector trajectories shown in FIG. 8D. While the source motion is the same for all three acquisition geometries, they are characterized by different increments of net detector motion (0, 25.0, and 50.0 mm).

Figure 16B:
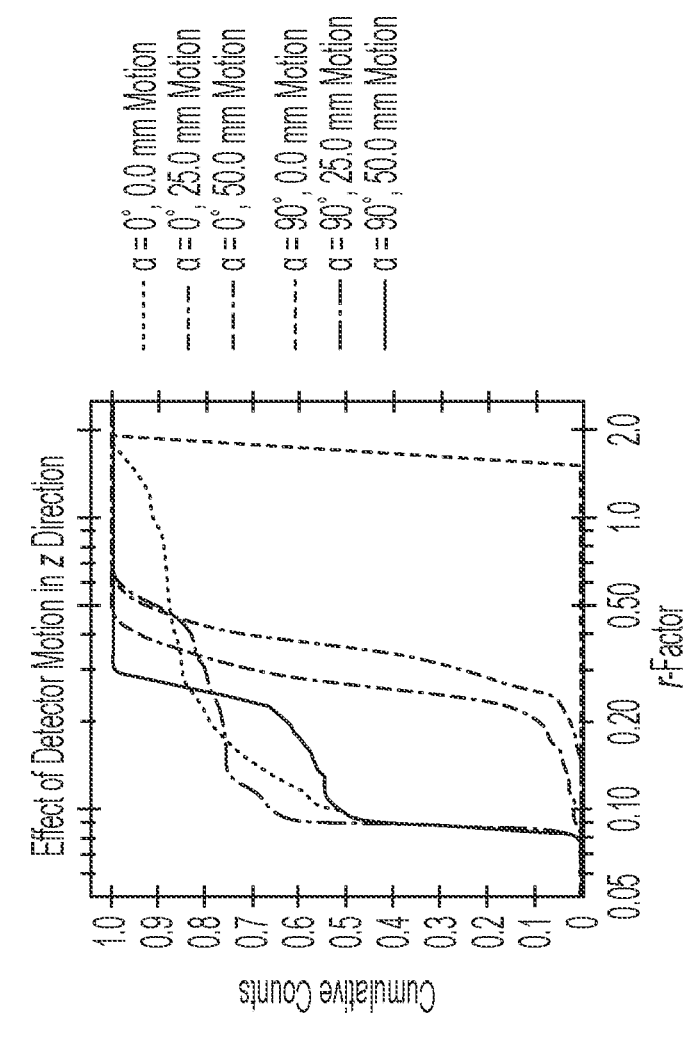
FIG. 16B is a graph depicting cumulative histograms of r-factor values obtained from 500 randomly sampled points in a volume of interest for two orientations of the input frequency and for the three detector trajectories shown in FIG. 8D according to aspects of the invention.
Figure 16A:
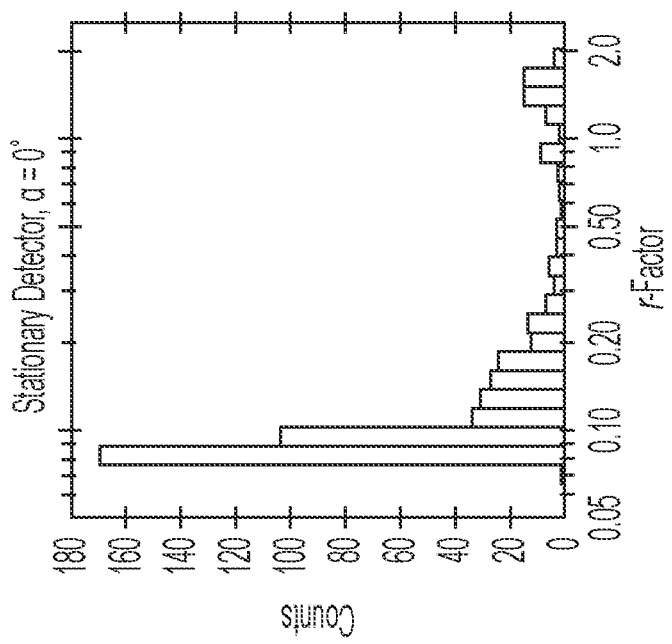
FIG. 16A is a graph depicting the histogram of r-factor values obtained from 500 randomly sampled points in a volume of interest for a tomosynthesis system with a stationary detector with the conventional acquisition geometry.

There are two polar angles considered in FIG. 16B to model different orientations of the input frequency. The 0° angle is analyzed first, corresponding to frequency oriented along the x direction. This direction is left-to-right in a CC view in a breast imaging application. As seen in FIG. 16A, the r-factor exceeds unity at 9.0% of the points if there is no detector motion. FIG. 16B demonstrates that by introducing detector motion along the z direction, super-resolution can be achieved at all points in the reconstruction, since the r-factor does not exceed unity at any point in the VOI. If 50.0 mm of net motion is used as opposed to 25.0 mm of net motion, the plateau is shifted further to the left, indicating an improvement in the r-factor.

The 90° polar angle is also analyzed in FIG. 16B. This orientation corresponds to frequency along the y direction. Along the y direction, there are no sub-pixel shifts in the image of an object between projections. For this reason, super-resolution cannot be achieved anywhere in the VOI, as the r-factor exceeds unity at all points. FIG. 16B indicates that by introducing detector motion along the z direction, the r-factor is below unity for all points in the VOI, and hence super-resolution is achieved everywhere.

To determine whether an acquisition geometry achieves super-resolution uniformly throughout the VOI, the 99th percentile of the cumulative histogram was calculated. Demonstrating that this percentile is well below unity ensures that at least 99% of the points in the reconstruction exhibit super-resolution with high quality. FIG. 16C illustrates how the 99th percentile varies among 200 bootstrapped simulations of 500 random points. For the purpose of this simulation, the detector is stationary and frequency is oriented along the 0° polar angle, similar to FIG. 16A.

The histogram shown in FIG. 16C can be used to calculate a 95% confidence interval ($CI_{95}$) for the 99th percentile. Since $CI_{95}$ varies between 1.60 and 1.82, FIG. 16C illustrates how the conventional design does not ensure super-resolution at a sufficiently large number of points in the VOI.

Figure 16D:
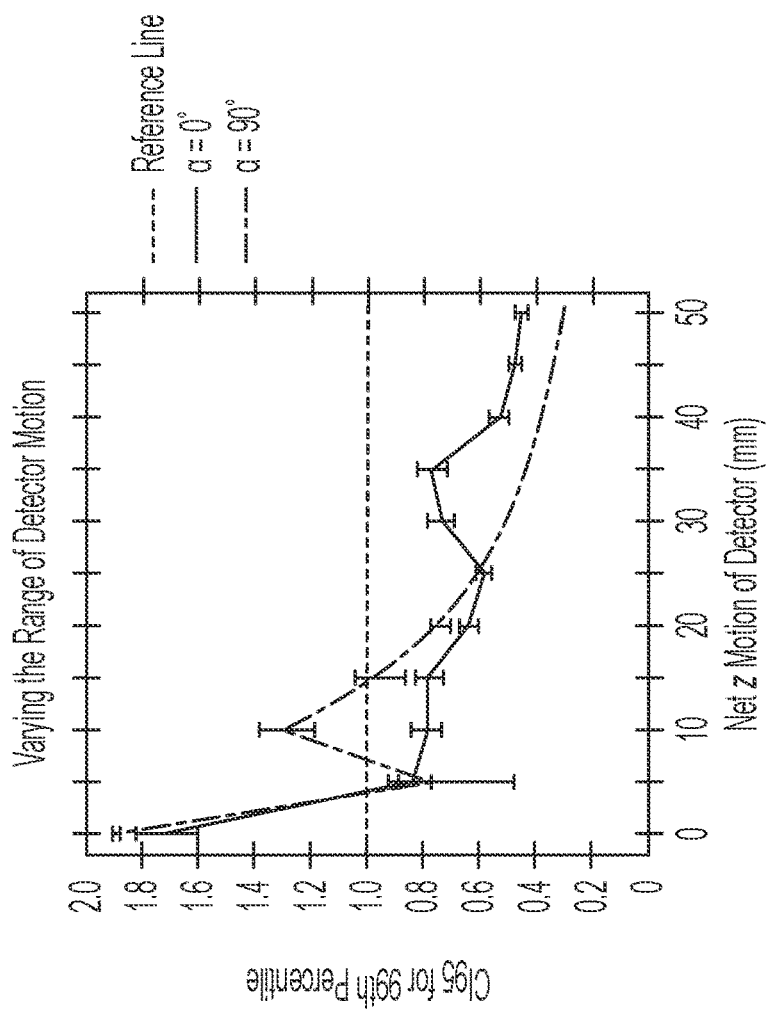
FIG. 16D is a graph of the bootstrapped 95% confidence interval for the $99^{th}$ percentile plotted as a function of the range of detector motion for two orientations of the input frequency according to aspects of the invention.
Figure 16C:
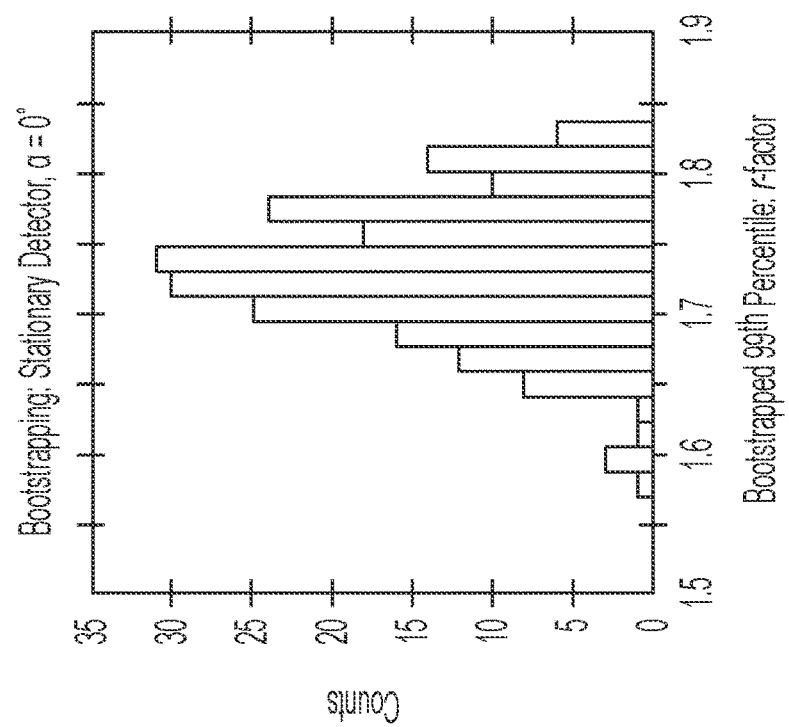
FIG. 16C is an illustration depicting how the $99^{th}$ percentile of the histogram of FIG. 16A varies among 200 bootstrapped simulations of 500 randomly sampled points in the volume of interest.

In FIG. 16D, it was analyzed how the $CI_{95}$ is impacted by the net increment of detector motion. For the purpose of this simulation, the detector position at the start of the scan ($b_{z1}$) is varied between −25.0 mm (net 0.0 mm motion) and −75.0 mm (net 50.0 mm motion). This simulation assumes that the detector position at the end of the scan ($b_{z2}$) is constant (−25.0 mm), as is the case in FIG. 8D. FIG. 16D demonstrates that detector motion along the z direction is necessary for ensuring that at least 99% of the points exhibit super-resolution.

The r-factor should be as small as possible to achieve super-resolution with high quality. In FIG. 16D, the lowest possible r-factor is achieved using 50.0 mm of net detector motion. With this design, the 95% confidence intervals are [0.425, 0.468] and [0.294, 0.306] for the 0° and 90° polar angles, respectively.

Example 6

For a breast imaging example, four acquisition geometries described in Table 1 are now analyzed.

TABLE 1

| Geometry | Source Motion | Detector Motion |
| --- | --- | --- |
| I | Linear (x) | None |
| II | Linear (x) | z Direction |
| III | T-Shaped (x and y) | None |
| IV | T-Shaped (x and y) | z Direction |

In all four geometries, it is assumed that $f_0=8.0$ mm$^{-1}$, $\varepsilon=0.50$ mm, $Q_x=200.0$ mm, and $b_{z2}=-25.0$ mm. In the geometries with detector motion (II and IV), it is assumed that the net motion along the z direction is 50.0 mm (i.e., $b_{z1}=-75.0$ mm). In the geometries with source motion along the PA direction (I and III), it is assumed that $Q_y=200.0$ mm and $N_x=N_y$.

Figure 17:
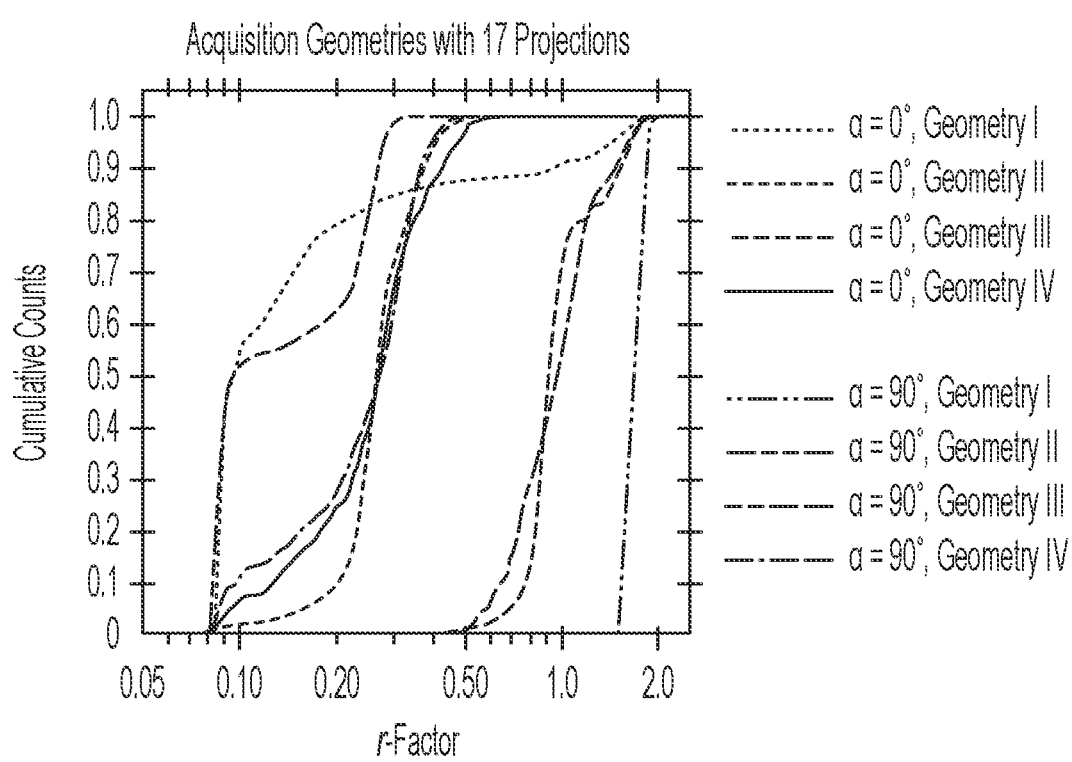
FIG. 17 is a graph illustrating cumulative histograms of the r-factor obtained from 500 randomly sampled points in a volume of interest for four acquisition geometries and two orientations of the input frequency in accordance with aspects of the invention.
Figure 18B:
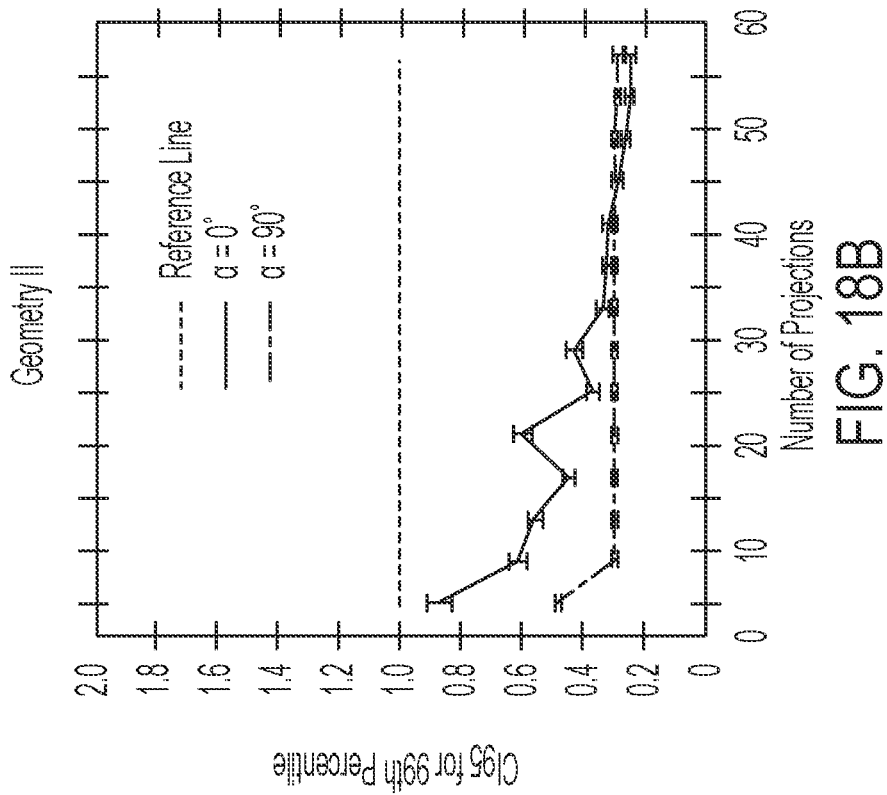
FIGS. 18A-18D are graphs of the bootstrapped 95% confidence interval for the $99^{th}$ percentile plotted as a function of the number of projections for the respective orientations and acquisition geometries of FIG. 17.
Figure 18A:
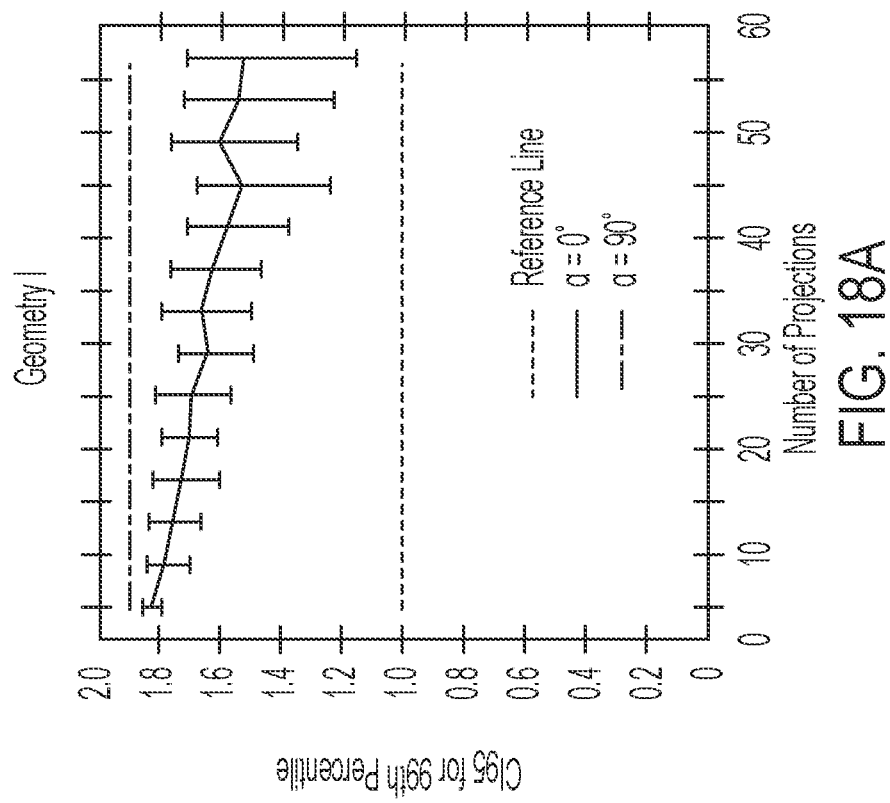
Figure 18D:
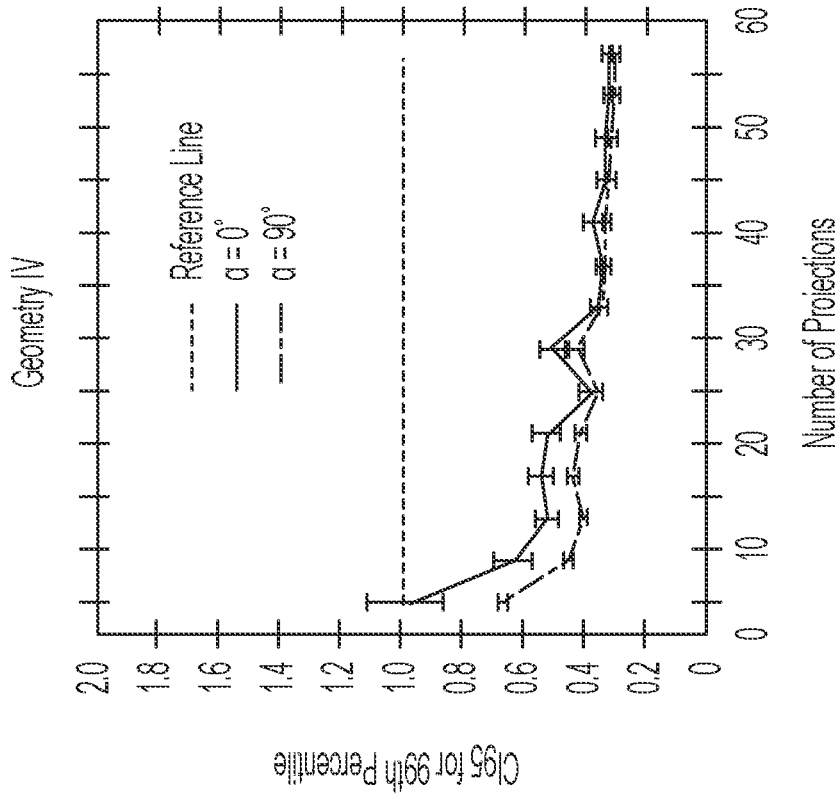
Figure 18C:
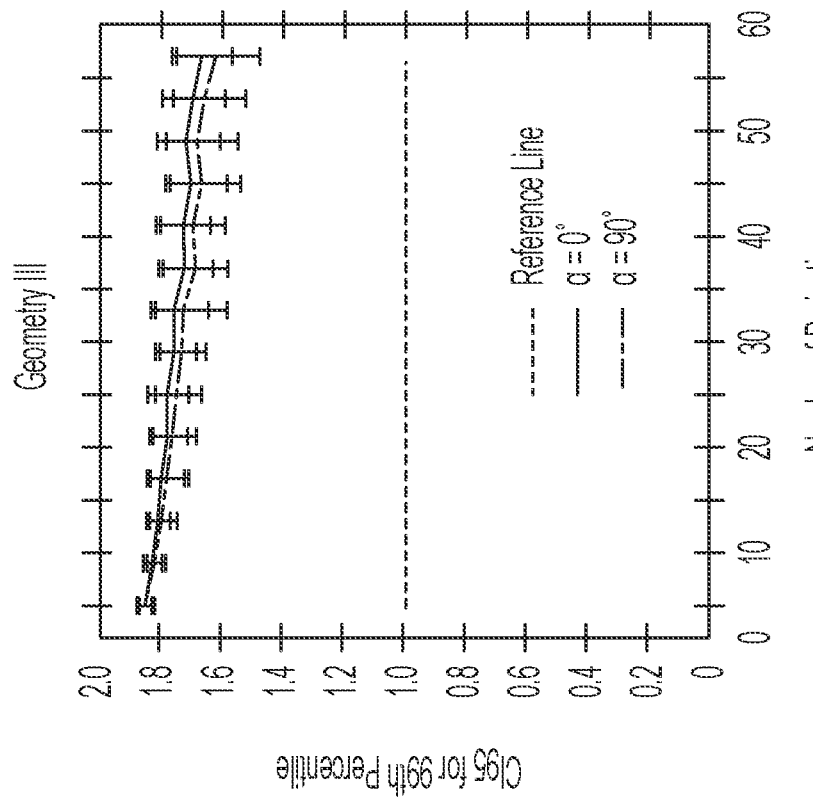
Figure 19B:
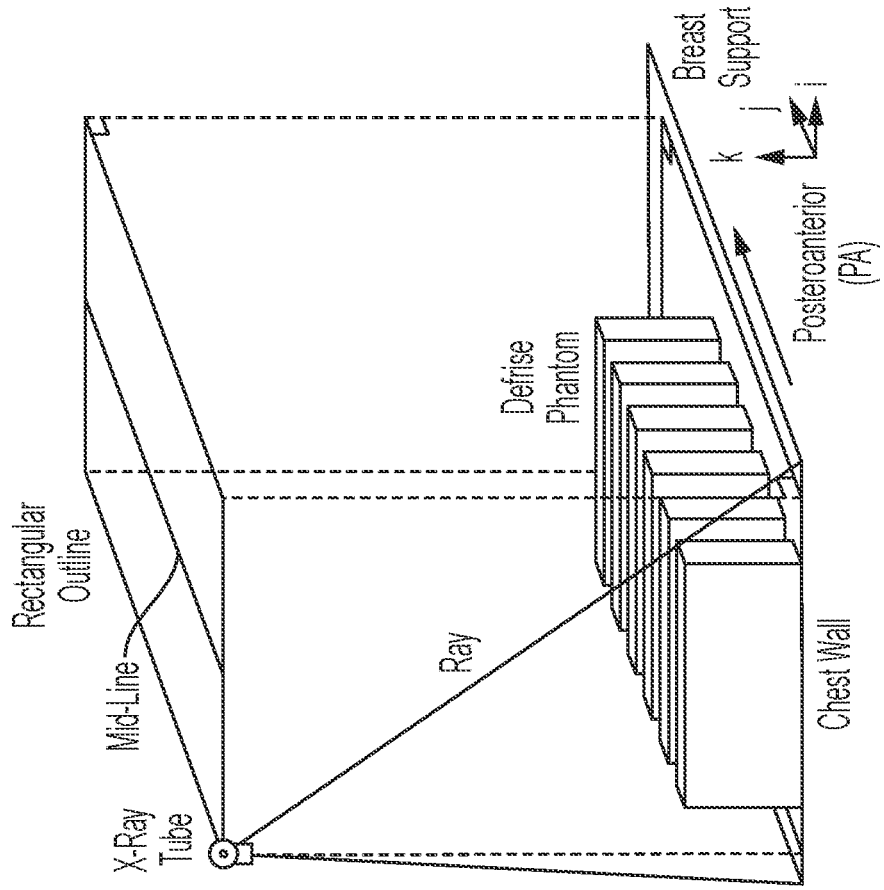
FIG. 19B is an illustration depicting an acquisition geometry with T-shaped source motion for imaging the Defrise phantom object of FIG. 19A according to aspects of the invention.
Figure 19A:
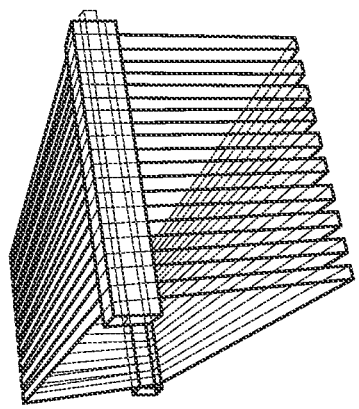
FIG. 19A is a photograph depicting a Defrise phantom object.
Figure 19D:
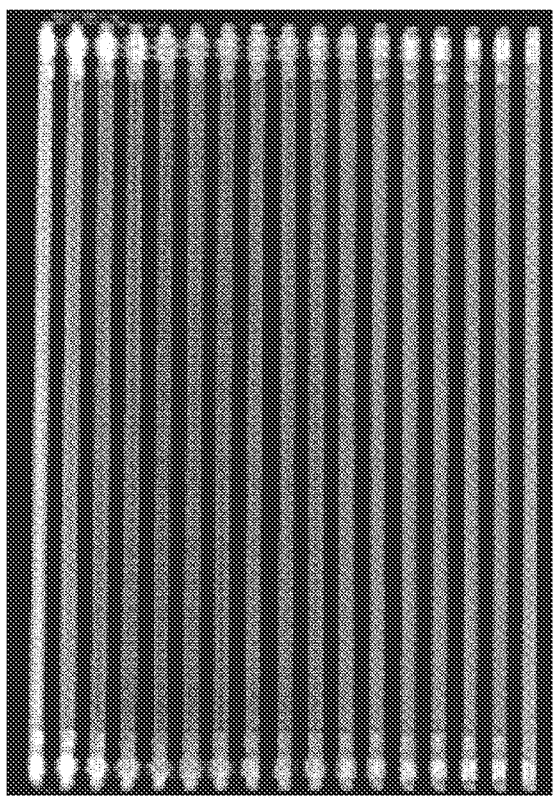
FIG. 19D is a reconstruction of a Defrise phantom obtained using a tomosynthesis acquisition geometry with T-shaped source motion in accordance with aspects of the invention.
Figure 19C:
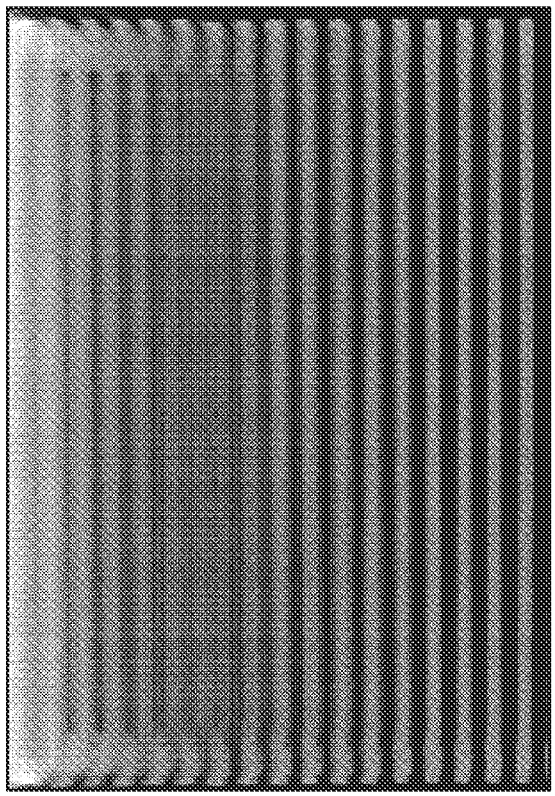
FIG. 19C is a reconstruction of a Defrise phantom obtained using a conventional tomosynthesis acquisition geometry.
Figure 19E:
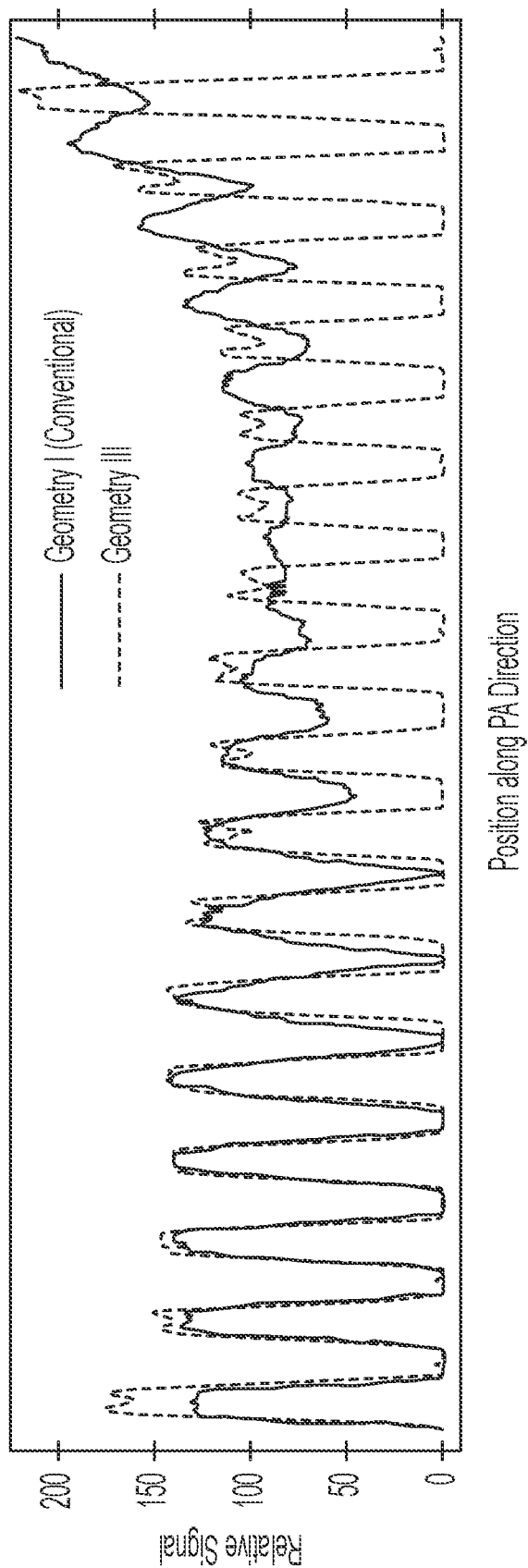
FIG. 19E is a graph of signal as a function of position in the reconstructions of FIGS. 19C and 19D.

Based on a random sample of 500 points in the VOI, the cumulative histograms of the r-factor are shown in FIG. 17 for the four geometries. For the purpose of this figure, it is assumed that there are 17 total projections in all four geometries.

One of the limitations of the conventional acquisition geometry (I) is that super-resolution is not achievable anywhere in the VOI if frequency is oriented along the 90° polar angle. FIG. 17 demonstrates that re-designing the source motion yields an improvement along this polar angle, since the r-factor is below unity at 53.8% of the points in the VOI (Geometry III).

To determine whether super-resolution is achieved uniformly throughout the VOI, the 99$^{th}$ percentile of each geometry should be analyzed, as in the previous Examples. One shortcoming of the geometries with a stationary detector (I and III) is that the 99$^{th}$ percentile exceeds unity, regardless of polar angle. Use of detector motion along the z direction ensures that the 99$^{th}$ percentile is below unity, yielding super-resolution at 99% of points in the VOI.

To quantify how image quality is impacted by the number of projections, FIGS. 18A-18D analyze the 99$^{th}$ percentile of the cumulative histogram as a function of $N_t$. Geometries with up to 57 projections were considered. With the exception of the variable $N_t$, this figure is prepared under the same assumptions as FIG. 17. For this reason, there are no changes to the net range of motion of the source and the detector. Consequently, as the number of projections is increased, there is finer spacing between source positions, and there is a smaller increment of detector translation per projection (geometries II and IV). We also continue to make the assumption that $N_x=N_y$ in considering geometries III and IV.

In the conventional acquisition geometry (I), the 95% confidence intervals are all above unity, regardless of polar angle. For this reason, it is not possible to achieve super-resolution at 99% of points in the VOI simply by increasing the number of projections. A similar result holds for geometry III.

To ensure that the 99$^{th}$ percentile is below unity, FIGS. 18A-18D illustrate that the system should be designed with either geometry II or geometry IV. While the trend is not perfectly monotonic, FIGS. 18B and 18D also demonstrate that the 99$^{th}$ percentile can be minimized by increasing the number of projections, yielding an improvement in the quality of super-resolution.

Example 7

Figures 20A, 20B, 20C:
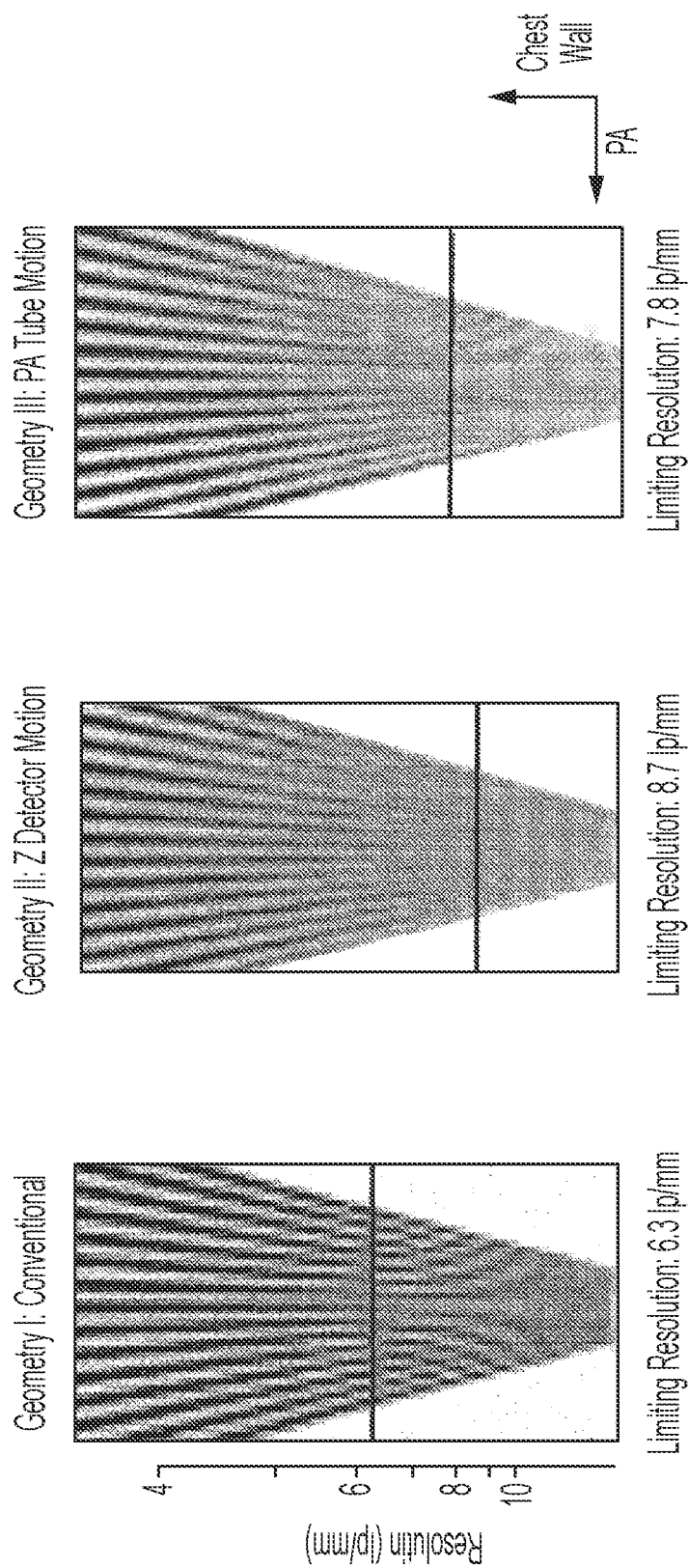
FIGS. 20A-20C are reconstructions of a star-pattern phantom in acquisition geometries with different trajectories for the source and detector according to aspects of the invention.

A prototype tomosynthesis system was constructed for research use at the University of Pennsylvania. The system illustrates different trajectories for the x-ray tube and detector in a breast imaging application. The detector element size is 0.085 mm, similar to Example 6. FIGS. 20A-20C show the limiting resolution along the PA direction for Geometry I (FIG. 20A), Geometry II (FIG. 20B) and Geometry III (FIG. 20C) As seen by comparing FIGS. 20A-20C, the highest resolution is achieved in the geometry with detector motion along the z direction (Geometry II, FIG. 20B).

Figure 21:
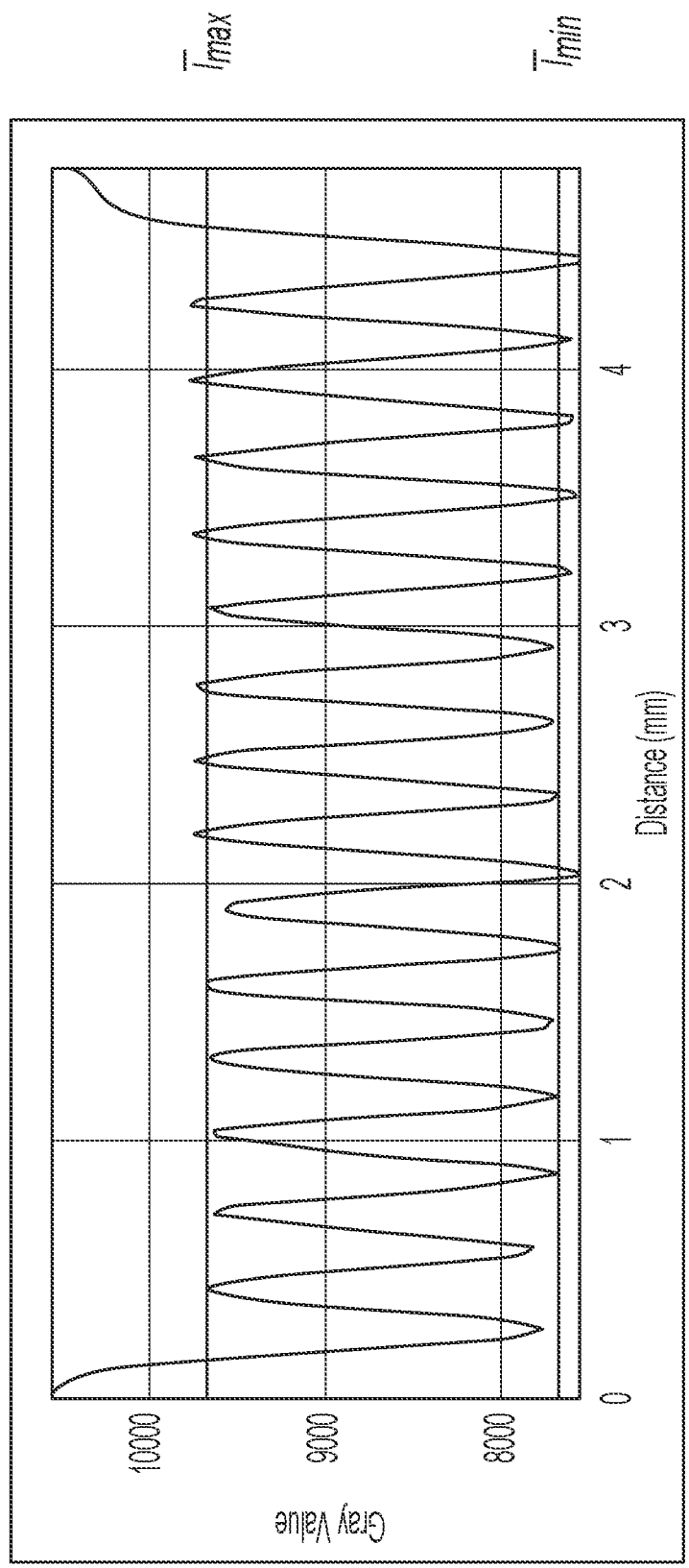
FIG. 21 is a graph of signal in the reconstruction of a star-pattern phantom illustrating the calculation of modulation contrast in accordance with aspects of the invention.
Figure 22A:
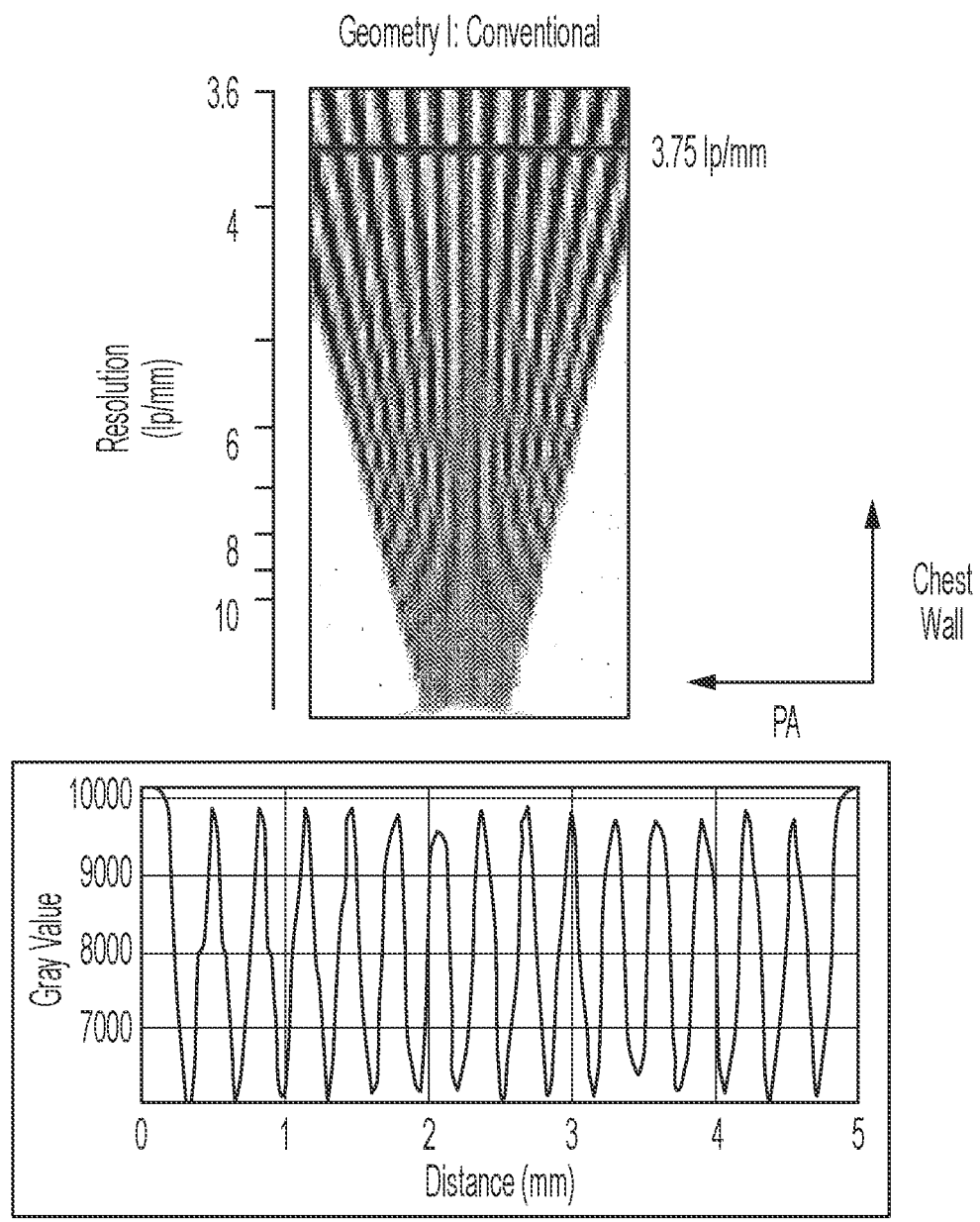
FIGS. 22A-22C are graphs of signal in the reconstruction of a star-pattern phantom at a frequency below the detector alias frequency for the respective acquisition geometries of FIGS. 20A-20C in accordance with aspects of the invention.
Figure 22B:
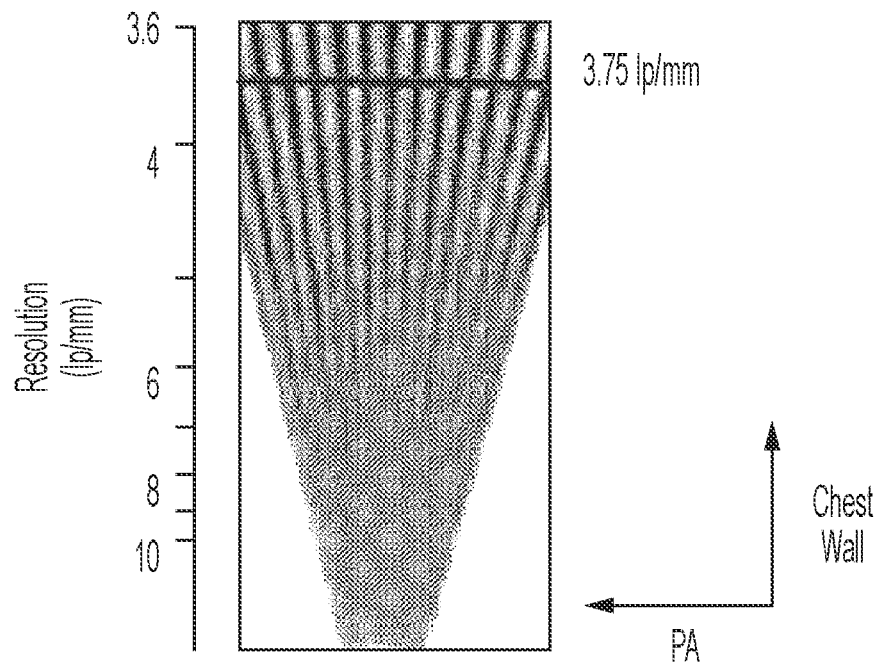
Figure 22B:
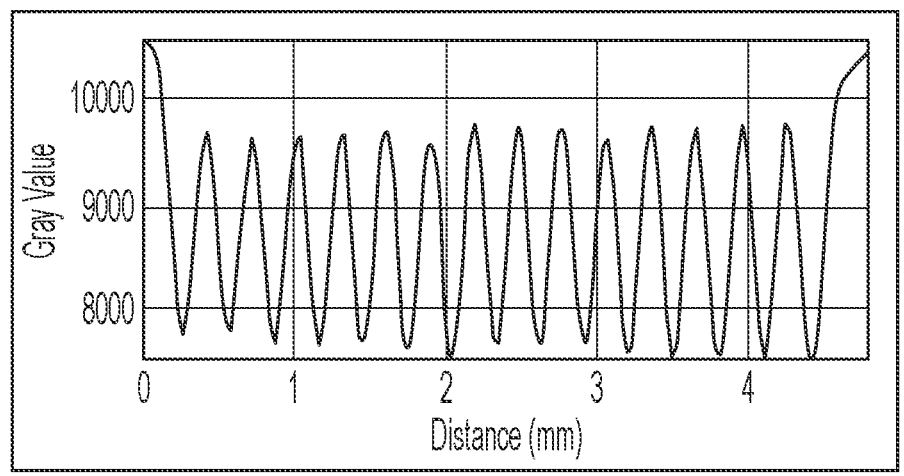
Figure 22C:
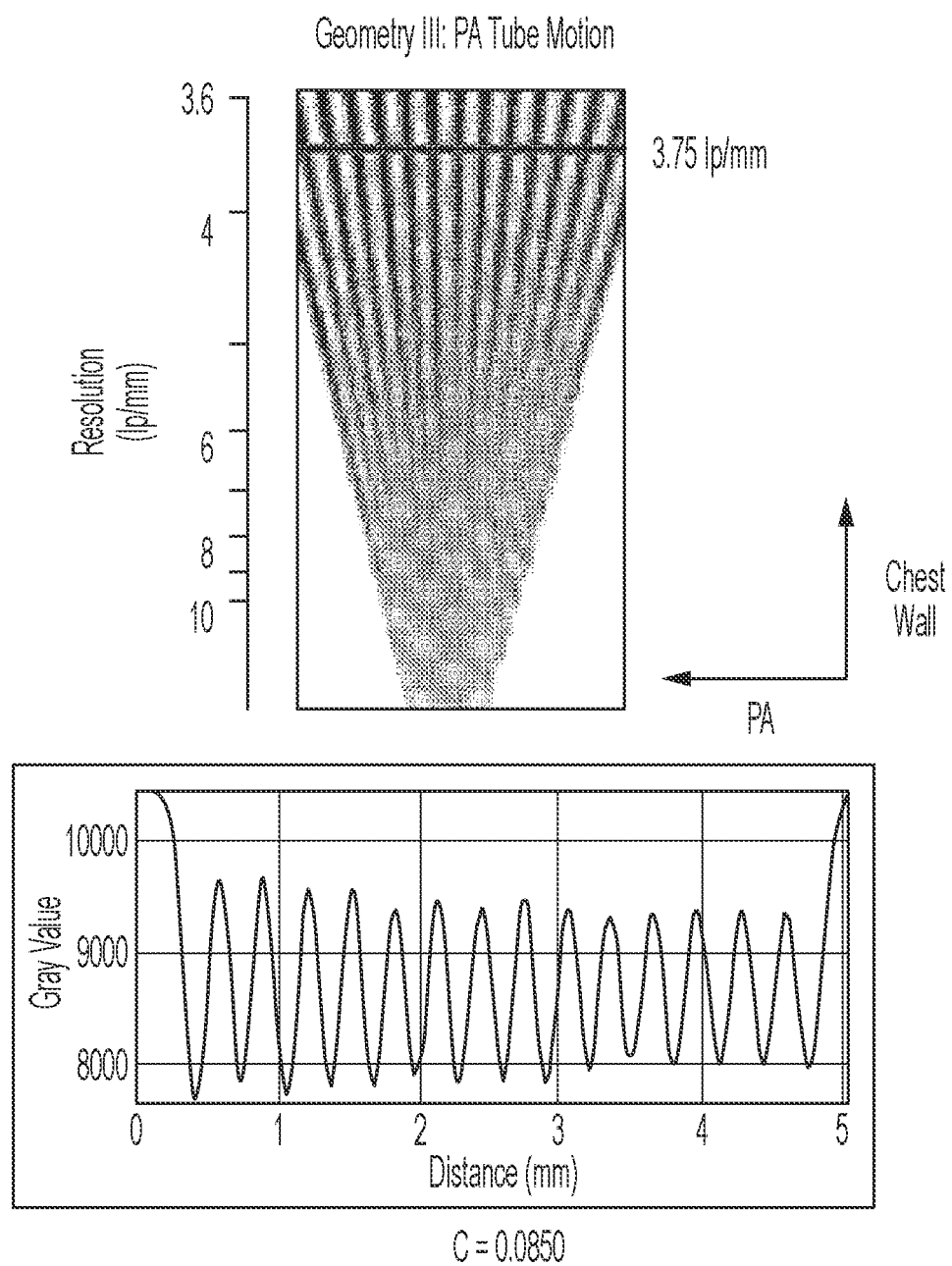

FIG. 21 illustrates a plot of signal as a function of position in the reconstruction. This graph can be used to calculate modulation contrast. FIGS. 22A-22C illustrate the calculation of modulation contrast at the frequency 3.75 mm$^{-1}$ in Geometries I, II, and III. This frequency is below the detector alias frequency (5.88 mm$^{-1}$).

Although the invention is illustrated and described herein with reference to specific embodiments, the invention is not intended to be limited to the details shown. Rather, various modifications may be made in the details within the scope and range of equivalents of the claims and without departing from the invention.

The invention claimed is:

1. A super-resolution digital tomosynthesis system for imaging an object, the system comprising:
    at least one source configured to emit penetrating particles toward the object;
    a detector configured to acquire a series of projection images of the object in response to the penetrating particles from the at least one source, the detector defining a plane of detection;
    one or more positioning elements configured to change a distance between the at least one source and the object by moving the at least one source, the object, the detector, or a combination thereof; and
    an imaging system configured to:
        control a position of the at least one source and the detector in relation to the object along a scan path using the one or more positioning elements to move the at least one source, the object, the detector, or a combination thereof;
        control the at least one source, the object, the detector, or a combination thereof to acquire a series of projection images along the scan path with a distance change between the at least one source, object, detector, or a combination thereof, wherein the distance between the at least one source, the object, the detector, or a combination thereof is changed due to the moving of the at least one source, the object, the detector, or a combination thereof such that a magnification of projected images of the series of projected images of the object detected by the detector varies as the at least one source travels along the scan path; and
        construct, based on the variations in the magnification of the projected images due to the movement of the at least one source, the object, the detector, or a combination thereof, a tomographic volume exhibiting super-resolution from data representing the acquired series of projection images.

2. The system of claim 1, wherein the distance between the at least one source, the object, the detector, or a combination thereof is varied over a range of values where a gain in super-resolution exceeds a detriment of focal spot blurring.

3. The system of claim 1, wherein the one or more positioning elements are configured to move the at least one source along the scan path and to move the object to change the distance between the at least one source and the object.

4. The system of claim 1, wherein the one or more positioning elements are configured to move the at least one source along the scan path and to move the at least one source and the detector to change the distance between the at least one source and the object.

5. The system of claim 1, wherein the distance between the at least one source, the object, the detector, or a combination thereof changes at a varying velocity.

6. The system of claim 1, wherein the distance between the locations of the at least one source varies so that there is a different increment of source motion per projection along the scan path.

7. The system of claim 1, wherein the distance between the at least one source and the object, along the scan path, varies so that there is a different increment of magnification per projection.

8. The system of claim 1, wherein the one or more positioning elements comprise:
    a first electromechanical drive coupled to the at least one source to move the at least one source along the scan path; and
    a second electromechanical drive coupled to the detector to change the distance between the detector and the object.

9. The system of claim 1, wherein the one or more positioning elements comprise:
    a first electromechanical drive coupled to the at least one source to move the at least one source along the scan path; and
    a second electromechanical drive coupled to the object to change the distance between the detector and the object.

10. The system of claim 1, wherein the one or more positioning elements comprise:
    a first electromechanical drive coupled to the at least one source to move the at least one source along the scan path; and
    a second electromechanical drive coupled to the object to change the distance between the detector and the object; and
    a third electromechanical drive coupled to the detector to change the distance between the at least one source, the detector, and the object.

11. The system of claim 1, wherein the detector is rotated to align with an orientation of the at least one source and the object as the orientation of the at least one source changes along the scan path, and the position of the object relative to the at least one source.

12. The system of claim 1, wherein the data representing the acquired series of projection images has super-resolution at every point in the tomographic volume.

13. The system of claim 1, wherein super-resolution comprises resolution that is finer than a physical size of detector elements used by the detector to capture each of the projection images of the series of projection images.

14. A super-resolution digital tomosynthesis method for imaging an object, the method comprising:
    positioning at least one source of penetrating particles along a scan path with respect to an object and a detector, the detector defining a plane of detection;
    changing a distance between the at least one source, the object, the detector, or a combination thereof as the at least one source is positioned along the scan path, wherein the distance between the at least one source, the object, the detector, or a combination thereof is changed by moving, using one or more positioning elements coupled to the at least one source, the object, the detector, or a combination thereof;
    acquiring a series of images along the scan path with a change of the distance between the at least one source, the object, the detector or a combination thereof, wherein the distance between the at least one source, the object, the detector, or a combination thereof is changed due to the moving of the source, the object, the detector, or a combination thereof such that a magnification of images of the series of images of the object detected by the detector varies as the at least one source travels along the scan path; and constructing, based on the variations in the magnification of the images of the series of images due to the movement of the at least one source, the object, the detector, or a combination thereof, a tomographic volume exhibiting super-resolution from data representing the acquired series of images.

15. The method of claim 14, further comprising displaying super-resolution images from the tomographic volume.

16. The method of claim 14, wherein the distance between the at least one source, the object, the detector, or a combination thereof is varied over a range of values where a gain in super-resolution exceeds a detriment of focal spot blurring.

17. The method of claim 14, wherein the data representing the acquired series of images has super-resolution at every point in the tomographic volume.

18. The method of claim 14, wherein the at least one source moves along the scan path and the detector moves while the at least one source moves along the scan path, to change the distance between the at least one source and the object.

19. The method of claim 14, wherein the at least one source moves along the scan path and the object moves while the at least one source moves along the scan path, to change the distance between the at least one source and the object.

20. The method of claim 14, wherein the at least one source moves along the scan path and the object and the detector moves while the at least one source moves along the scan path, to change the distance between the more or more sources and the object.

21. The method of claim 14, wherein the detector is moved in a direction at least substantially perpendicular to a surface of the detector.

22. The method of claim 14, wherein the distance between the at least one source, the object and the detector changes at a varying velocity.

23. The method of claim 14, wherein the distance between the one or more source locations along the scan path varies so that there is a different increment of detector motion per projection.

24. The method of claim 14, wherein the distance between the one or more source locations and the object, along the scan path of the at least one source, varies so that there is a different magnification of the object for each projection.

* * * * *